(12) United States Patent
Pratt et al.

(10) Patent No.: US 11,649,493 B1
(45) Date of Patent: May 16, 2023

(54) METHODS AND SYSTEMS FOR NUCLEIC ACID SEQUENCING

(71) Applicant: Ultima Genomics, Inc., Newark, CA (US)

(72) Inventors: Mark Pratt, Bozeman, MT (US); Florian Oberstrass, Menlo Park, CA (US); Linda Lee, Palo Alto, CA (US); Steven Menchen, Fremont, CA (US)

(73) Assignee: ULTIMA GENOMICS, INC., Newark, CA (US)

( * ) Notice: Subject to any disclaimer, the term of this patent is extended or adjusted under 35 U.S.C. 154(b) by 892 days.

(21) Appl. No.: 16/525,826

(22) Filed: Jul. 30, 2019

Related U.S. Application Data

(60) Provisional application No. 62/712,872, filed on Jul. 31, 2018.

(51) Int. Cl.
*C12Q 1/6874* (2018.01)

(52) U.S. Cl.
CPC ...... *C12Q 1/6874* (2013.01); *C12Q 2535/113* (2013.01); *C12Q 2537/155* (2013.01); *C12Q 2537/157* (2013.01); *C12Q 2549/10* (2013.01); *C12Y 207/07007* (2013.01)

(58) Field of Classification Search
None
See application file for complete search history.

(56) References Cited

U.S. PATENT DOCUMENTS

| 5,409,811 | A | 4/1995 | Tabor et al. |
| 5,674,716 | A | 10/1997 | Tabor et al. |
| 2018/0305749 | A1* | 10/2018 | Stromberg ........... C12Q 1/6874 |

OTHER PUBLICATIONS

Betz, et al. KlenTaq polymerase replicates unnatural base pairs by inducing a Watson-Crick geometry. Nat Chem Biol 8:612-614 (2012).

Tabor, et al. A single residue in DNA polymerases of the *Escherichia coli* DNA polymerase I family is critical for distinguishing between deoxy-and dideoxyribonucleotides. Proc. Natl. Acad. Sci. USA, 92:6339-6343, 1995.

Tabor, et al., Effect of manganese ions on the incorporation of dideoxynucleotides by bacteriophage T7 DNA polymerase and *Escherichia coli* DNA polymerase I, Proc. Natl. Acad. Sci. USA, Jun. 1989, 86:4076-80.

* cited by examiner

*Primary Examiner* — Teresa E Strzelecka
(74) *Attorney, Agent, or Firm* — Wilson Sonsini Goodrich & Rosati

(57) ABSTRACT

The present disclosure provides methods and systems for processing a nucleotide mixture. A nucleotide mixture can be purified. A nucleotide mixture can be processed for use in nucleic acid synthesis. A nucleotide mixture can be processed for use in nucleic acid sequencing.

19 Claims, 12 Drawing Sheets

METHODS AND SYSTEMS FOR NUCLEIC ACID SEQUENCING

CROSS-REFERENCE

This application claims the benefit of U.S. Provisional Patent Application No. 62/712,872, filed Jul. 31, 2018, which application is entirely incorporated herein by reference for all purposes.

BACKGROUND

Next generation nucleic acid (e.g., DNA) sequencing technologies, such as sequencing by synthesis, may allow for rapid sequencing of target nucleic acids in a wide variety of applications. These technologies may use reagents such as nucleotides or nucleotide analogs to synthesize a nucleic acid molecule from a target, thereby determining of a sequence for the target. Determining the sequence of a target may comprise the use of labeled (e.g., fluorescently labeled) nucleotides or nucleotide analogs to determine the sequence of a target.

SUMMARY

As recognized herein, sequencing may require the use of nucleotide or nucleotide analog solutions, where each solution contains only a single canonical type of nucleotide or nucleotide analog (e.g., A, T, G, C, U) or less than all types of nucleotides or nucleotide analogs. Small amounts of undesired nucleotide or nucleotide analog in a given solution may corrupt data from clonal colonies, such as by phasing. This may occur when inappropriate nucleotides incorporate into an ongoing synthesis strand, resulting in a strand which is out of phase. As such, the requirement for purity in a nucleotide or nucleotide analog reagent solution may be important. Reagents may suffer little depletion of nucleotides or nucleotide analogs in a single cycle of incorporation; however the purity requirements may prevent the reuse of reagents, increasing the cost of sequencing. Recognized herein is a need for methods and systems for processing a nucleotide solution which enable improved reagent purity. Also recognized herein is a need for methods and systems for nucleic acid sequencing which allow for improved sequencing quality (e.g., reduction in phasing rate) while reducing cost.

In one aspect, the present disclosure provides a method for processing a plurality of nucleic acid molecules, comprising: (a) directing a plurality of nucleotides or nucleotide analogs to a first reaction space comprising a support having a first plurality of nucleic acid molecules immobilized thereto; (b) incorporating a subset of nucleotides or nucleotide analogs from the plurality of nucleotides or nucleotide analogs into the first plurality of nucleic acid molecules, thereby providing a remainder of the plurality of nucleotides or nucleotides analogs, wherein (b) is performed in absence of detecting the subset of nucleotides incorporated into the plurality of nucleic acid molecules; (c) bringing the remainder of the plurality of nucleotides or nucleotides analogs in contact with a second plurality of nucleic acid molecules in a second reaction space; and (d) incorporating at least a subset of the remainder of the plurality of nucleotides or nucleotides analogs into the second plurality of nucleic acid molecules. In some embodiments, the method further comprises detecting the incorporation of the at least the subset of the remainder of the plurality of nucleotides or nucleotide analogs into the second plurality of nucleic acid molecules. In some embodiments, the subset comprises nucleotides or nucleotide analogs of one or more but less than all canonical types. In some embodiments, the subset consists of nucleotides or nucleotide analogs of one, two, or three canonical types.

In some embodiments, the method further comprises determining a sequence of at least one of the second plurality of nucleic acid molecules subsequent to (d). In some embodiments, determining the sequence is performed at a phasing rate of at most 1% for a sequence of the nucleic acid molecule having a length of at least 50 nucleic acid bases in absence of resequencing the nucleic acid molecule. In some embodiments, the phasing rate is at most 0.1%. In some embodiments, the phasing rate is at most 0.01%. In some embodiments, the length is at least 100 nucleotides. In some embodiments, the length is at least 200 nucleotides. In some embodiments, the length is at least 500 nucleotides. In some embodiments, (b) is performed in absence of determining a sequence for any of the first plurality of nucleic acid molecules.

In some embodiments, the subset of nucleotides or nucleotide analogs is incorporated using a nucleic acid polymerizing enzyme. In some embodiments, the nucleic acid polymerizing enzyme is a deoxyribonucleic acid polymerizing enzyme. In some embodiments, the nucleic acid polymerizing enzyme is phi29 polymerase, Bst 3.0 polymerase, or a variant thereof. In some embodiments, the first plurality of nucleic acid molecules are circular nucleic acid molecules, and wherein the nucleic acid polymerizing enzyme is capable of strand displacement. In some embodiments, the first plurality of nucleic acid molecules contains nucleotides complementary to the subset of nucleotides or nucleotide analogs. In some embodiments, the first plurality of nucleic acid molecules contains a greater number of nucleotides complementary to the subset of nucleotides or nucleotide analogs relative to all other nucleotides. In some embodiments, the first plurality of nucleic acid molecules does not contain nucleotides that are not complementary to the subset of nucleotides or nucleotide analogs.

In some embodiments, the subset of nucleotides or nucleotide analogs comprises less than 10%, less than 5%, less than 1%, less than 0.1%, or less than 0.01% of the plurality of nucleotides or nucleotide analogs. In some embodiments, a nucleic acid molecule of the first plurality of nucleic acid molecules comprises a priming site. In some embodiments, the priming site is a primer covalently coupled to the nucleic acid molecule. In some embodiments, the plurality of nucleotides or nucleotide analogs include deoxynucleotides. In some embodiments, the plurality of nucleotides or nucleotide analogs include dideoxynucleotides. In some embodiments, the plurality of nucleotides or nucleotide analogs comprises nucleotides or nucleotide analogs selected from the group consisting of deoxyadenosine triphosphate (dATP), 2',3'-ideoxyadenosine-5'triphosphate (ddATP), deoxyguanosine triphosphate (dGTP), 2',3'-dideoxyguanosine-5'-triphosphate (ddGTP), deoxycytidine triphosphate (dCTP), 2',3'-dideoxycytidine-5'-triphosphate (ddCTP), deoxythymidine triphosphate (dTTP), 2',3'-dideoxythymidine-5'-triphosphate (ddTTP), deoxyuridine triphosphate (dUTP), 2',3'-dideoxyuridine-5'-triphosphate (ddUTP), and a variant thereof. In some embodiments, the subset of nucleotides or nucleotide analogs includes bases of a different type from the remainder of the plurality of nucleotides or nucleotide analogs. In some embodiments, incorporating the subset of nucleotides or nucleotide analogs into the first plurality of nucleic acid molecules yields the remainder of the plurality of nucleotides or nucleotides analogs having a purity that is increased relative to a purity of the plurality of nucleotides or nucleotide analogs.

In some embodiments, the support is a solid support. In some embodiments, the support is a polymer matrix. In some embodiments, the support is a particle. In some embodiments, the particle is a bead. In some embodiments, the particle is a gel particle. In some embodiments, the gel particle is an aerogel particle. In some embodiments, the gel particle is a hydrogel particle. In some embodiments, the support comprises a fiberglass structure. In some embodiments, the support comprises at least one planar surface. In some embodiments, the first reaction space and the second reaction space are the same reaction space.

In some embodiments, the incorporating in (b) yields double stranded nucleic acid molecules from the first plurality of nucleic acid molecules comprising the subset of nucleotides or nucleotide analogs, and wherein, subsequent to (b), the first reaction space is replenished with an additional plurality of nucleic acid molecules, which additional plurality of nucleic acid molecules does not include the subset of nucleotides or nucleotide analogs. In some embodiments, the first reaction space is replenished by directing an additional support with the additional plurality of nucleic acid molecules to the first reactions space. In some embodiments, the support is a polymer matrix. In some embodiments, the support is a particle. In some embodiments, the particle is a bead. In some embodiments, the particle is a gel particle. In some embodiments, the gel particle is an aerogel particle. In some embodiments, the gel particle is a hydrogel particle. In some embodiments, the support comprises a fiberglass structure.

In some embodiments, the first reaction space is replenished by denaturation of the double stranded nucleic acid molecules and removal of resultant single stranded nucleic acid molecules that are not immobilized to the support. In some embodiments, the denaturation is chemical denaturation. In some embodiments, the denaturation is thermal denaturation. In some embodiments, removal of the single stranded nucleic acid molecules comprises washing, filtering, or a combination thereof. In some embodiments, the first reaction space is further replenished with a plurality of nucleic acid polymerizing enzymes.

In some embodiments, the sequence of the nucleic acid molecule is determined by detecting one or more signals from the nucleic acid molecule upon incorporation of the at least the subset of the remainder of the plurality of nucleotides or nucleotides analogs into the nucleic acid molecule. In some embodiments, the at least the subset of the remainder of the plurality of nucleotides or nucleotide analogs is incorporated using a nucleic acid polymerizing enzyme. In some embodiments, the nucleic acid polymerizing enzyme is a deoxyribonucleic acid polymerizing enzyme. In some embodiments, the deoxyribonucleic acid polymerizing enzyme is phi-29 polymerase, Bst 3.0 polymerase, or a variant thereof. In some embodiments, the signals are optical signals. In some embodiments, the optical signals are detected with an optical detector. In some embodiments, the signals are charge changes. In some embodiments, the charge changes are detected with an ion sensor, voltage sensor, or combination thereof.

In some embodiments, the method further comprises repeating (a)-(d) with at least one additional plurality of nucleotides or nucleotide analogs. In some embodiments, the at least one additional plurality of nucleotides or nucleotide analogs comprises nucleotides or nucleotide analogs from the remainder of the plurality of nucleotides or nucleotides analogs. In some embodiments, the remainder of the plurality of nucleotides or nucleotide analogs has a ratio of a number of nucleotides or nucleotide analogs of one or more but less than all canonical types to a number of nucleotides or nucleotide analogs of all other canonical types which is greater than 19:1. In some embodiments, the ratio is at least 29:1. In some embodiments, the ratio is at least 99:1. In some embodiments, the ratio is at least 999:1.

In one aspect, the present disclosure provides a method for processing a mixture, comprising: (a) selecting from a set of canonical types of nucleotides or nucleotides analogs a subset of canonical types of nucleotides or nucleotide analogs; (b) directing a mixture comprising a plurality of nucleotides or nucleotide analogs to a reaction space comprising a support having a plurality of nucleic acid molecules immobilized thereto, wherein a percentage of nucleotides or nucleotide analogs corresponding to the subset relative to all other nucleotides or nucleotide analogs in the mixture is greater than 50%; and (c) incorporating nucleotides or nucleotide analogs from the mixture that do not correspond to the subset into the plurality of nucleic acid molecules such that the percentage is increased following the incorporating; wherein (a)-(c) are performed in absence of sequencing or sequence identification of the plurality of nucleic acid molecules. In some embodiments, in (b), the percentage is greater than 80%, greater than 90%, greater than 95%, greater than 99%, greater than 99.9%, or greater than 99.99%. In some embodiments, in (c), the percentage is increased by at least tenfold. In some embodiments, in (c), the percentage is increased by at least a hundredfold. In some embodiments, in (c), the percentage is increased by at least a thousandfold.

In one aspect, the present disclosure provides a method for processing a mixture, comprising: (a) selecting from a set of canonical types of nucleotides or nucleotides analogs a subset of canonical types of nucleotides or nucleotide analogs; (b) directing a mixture comprising a plurality of nucleotides or nucleotide analogs to a reaction space comprising a support having a plurality of nucleic acid molecules immobilized thereto, wherein a percentage of nucleotides or nucleotide analogs corresponding to the subset relative to all other nucleotides or nucleotide analogs in the mixture is less than 20%; and (c) incorporating nucleotides or nucleotide analogs from the mixture corresponding to the subset into the plurality of nucleic acid molecules such that the percentage is reduced following incorporation, wherein (a)-(c) are performed in absence of sequencing or sequence identification of the plurality of nucleic acid molecules. In some embodiments, in (b), the percentage is less than 10%, less than 5%, less than 1%, less than 0.1%, or less than 0.01%. In some embodiments, in (c), the percentage is reduced by at least tenfold. In some embodiments, in (c), the percentage is reduced by at least a hundredfold. In some embodiments, in (c), the percentage is reduced by at least a thousandfold.

In some embodiments, the (c) is performed using a nucleic acid polymerizing enzyme. In some embodiments, the nucleic acid polymerizing enzyme is a deoxyribonucleic acid polymerizing enzyme. In some embodiments, the plurality of nucleic acid molecules are circular nucleic acid molecules, and wherein the nucleic acid polymerizing enzyme is capable of strand displacement. In some embodiments, the nucleic acid polymerizing enzyme is phi29 polymerase, Bst 3.0 polymerase, or a variant thereof. In some embodiments, the first plurality of nucleic acid molecules are circular nucleic acid molecules, and wherein the nucleic acid polymerizing enzyme is capable of strand displacement. In some embodiments, the plurality of nucleic acid molecules contains nucleotides complementary to the canonical types of nucleotides or nucleotide analogs of the subset. In some embodiments, the plurality of nucleic acid molecules contains a greater number of nucleotides complementary to the canonical types of nucleotides or nucleotide analogs of the subset relative to all other nucleotides. In some embodiments, the plurality of nucleic acid molecules does not contain nucleotides that are not complementary to the canonical types of nucleotides or nucleotide analogs of the subset. In some embodiments, a nucleic acid molecule of the plurality of nucleic acid molecules comprises a priming site. In some embodiments, the priming site is a primer covalently coupled to the nucleic acid molecule.

In some embodiments, the plurality of nucleotides or nucleotide analogs includes deoxynucleotides. In some embodiments, the plurality of nucleotides or nucleotide analogs includes dideoxynucleotides. In some embodiments, the plurality of nucleotides or nucleotide analogs comprises nucleotides or nucleotide analogs selected from the group consisting of deoxyadenosine triphosphate (dATP), 2',3'-ideoxyadenosine-5'triphosphate (ddATP), deoxyguanosine triphosphate (dGTP), 2',3'-dideoxyguanosine-5'-triphosphate (ddGTP), deoxycytidine triphosphate (dCTP), 2',3'-dideoxycytidine-5'-triphosphate (ddCTP), deoxythymidine triphosphate (dTTP), 2',3'-dideoxythymidine-5'-triphosphate (ddTTP), deoxyuridine triphosphate (dUTP), 2',3'-dideoxyuridine-5'-triphosphate (ddUTP), and a variant thereof. In some embodiments, the support is a solid support. In some embodiments, the support is a polymer matrix. In some embodiments, the support is a particle. In some embodiments, the particle is a bead. In some embodiments, the particle is a gel particle. In some embodiments, the gel particle is an aerogel particle. In some embodiments, the gel particle is a hydrogel particle.

In some embodiments, the support comprises a fiberglass structure. In some embodiments, the support comprises at least one planar surface.

In some embodiments, the incorporating in (c) yields double stranded nucleic acid molecules from the plurality of nucleic acid molecules comprising nucleotides or nucleotide analogs corresponding to the subset, and wherein, subsequent to (c), the reaction space is replenished with an additional plurality of nucleic acid molecules, which additional plurality of nucleic acid molecules does not include the nucleotides or nucleotide analogs incorporated in (c). In some embodiments, the reaction space is replenished by directing an additional support with the additional plurality of nucleic acid molecules to the first reactions space. In some embodiments, the support is a polymer matrix. In some embodiments, the support is a particle. In some embodiments, the particle is a bead. In some embodiments, the particle is a gel particle. In some embodiments, the gel particle is an aerogel particle. In some embodiments, the gel particle is a hydrogel particle. In some embodiments, the support comprises a fiberglass structure.

In some embodiments, the reaction space is replenished by denaturation of the double stranded nucleic acid molecules and removal of resultant single stranded nucleic acid molecules that are not immobilized to the support. In some embodiments, the denaturation is chemical denaturation. In some embodiments, the denaturation is thermal denaturation. In some embodiments, removal of the single stranded nucleic acid molecules comprises washing, filtering, or a combination thereof. In some embodiments, the first reaction space is further replenished with a plurality of nucleic acid polymerizing enzymes.

In one aspect, the present disclosure provides a method for synthesizing a nucleic acid molecule, comprising: (a) directing a plurality of nucleotides or nucleotide analogs to a first reaction space comprising a support having a plurality of nucleic acid molecules immobilized thereto; (b) incorporating a subset of nucleotides or nucleotide analogs from the plurality of nucleotides or nucleotide analogs into the plurality of nucleic acid molecules, thereby providing a remainder of the plurality of nucleotides or nucleotides analogs; and (c) using the remainder of the plurality of nucleotides or nucleotide analogs to perform nucleic acid synthesis, thereby synthesizing the nucleic acid molecule; wherein (a)-(b) are performed in absence of sequencing or sequence identification of the plurality of nucleic acid molecules. In some embodiments, the subset comprises nucleotides or nucleotide analogs of one or more but less than all canonical types. In some embodiments, the subset consists of nucleotides or nucleotide analogs of one, two, or three canonical types. In some embodiments, the nucleic acid synthesis comprises nucleic acid sequencing. In some embodiments, canonical types in the subset of nucleotides or nucleotide analogs are mutually exclusive from canonical types of the remainder in the plurality of nucleotides or nucleotide analogs. In some embodiments, the subset of nucleotides or nucleotide analogs is incorporated using a nucleic acid polymerizing enzyme.

In some embodiments, the nucleic acid polymerizing enzyme is a deoxyribonucleic acid polymerizing enzyme. In some embodiments, the nucleic acid polymerizing enzyme is phi29 polymerase or Bst 3.0 polymerase. In some embodiments, the plurality of nucleic acid molecules are circular nucleic acid molecules, and wherein the nucleic acid polymerizing enzyme is capable of strand displacement. In some embodiments, the plurality of nucleic acid molecules contains nucleotides complementary to the subset of nucleotides or nucleotide analogs. In some embodiments, the subset of nucleotides or nucleotide analogs comprises less than 10% of the plurality of nucleotides or nucleotide analogs. In some embodiments, the plurality of nucleic acid molecules contains nucleotides complementary to the subset of nucleotides or nucleotide analogs. In some embodiments, the plurality of nucleic acid molecules contains a greater number of nucleotides complementary to the subset of nucleotides or nucleotide analogs relative to all other nucleotides. In some embodiments, the plurality of nucleic acid molecules does not contain nucleotides that are not complementary to the subset of nucleotides or nucleotide analogs.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

DETAILED DESCRIPTION

Figure 1:
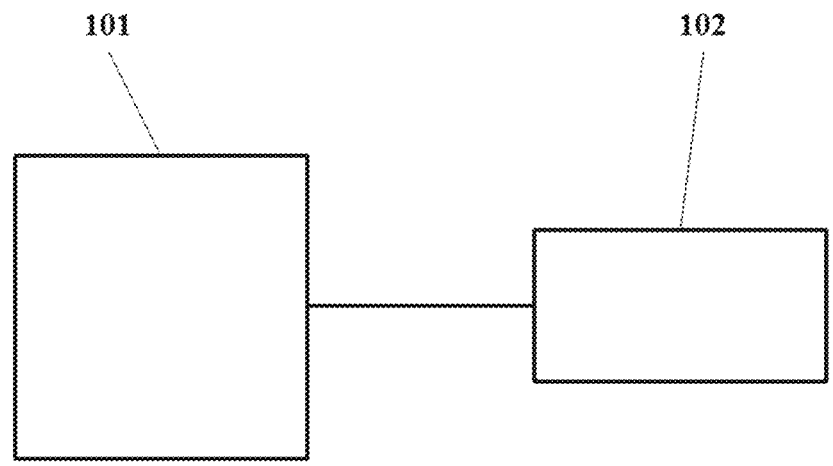
FIG. 1 shows a system of the present disclosure comprising a first reaction space and a second reaction space.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The terms "amplifying," "amplification," and "nucleic acid amplification" are used interchangeably and generally refer to generating one or more copies of a nucleic acid molecule. For example, "amplification" of deoxyribonucleic acid (DNA) generally refers to generating one or more copies of a DNA molecule. Moreover, amplification of a nucleic acid may linear, exponential, or a combination thereof. Amplification may be emulsion based or may be non-emulsion based. Non-limiting examples of nucleic acid amplification methods include reverse transcription, primer extension, polymerase chain reaction (PCR), ligase chain reaction (LCR), helicase-dependent amplification, asymmetric amplification, rolling circle amplification, and multiple displacement amplification (MDA). Where PCR is used, any form of PCR may be used, with non-limiting examples that include real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, mini-primer PCR, multiplex PCR, nested PCR, overlap-extension PCR, thermal asymmetric interlaced PCR and touchdown PCR. PCR may be performed with thermal cycling through one or more heating and cooling cycles. Alternatively, PCR may be performed isothermally. Moreover, amplification can be conducted in a reaction mixture comprising various components (e.g., a primer(s), template, nucleotides, a polymerase, buffer components, co-factors, etc.) that participate or facilitate amplification. In some cases, the reaction mixture comprises a buffer that permits context independent incorporation of nucleotides. Non-limiting examples include magnesium-ion, manganese-ion and isocitrate buffers. Additional examples of such buffers are described in Tabor, S. et al. C.C. PNAS, 1989, 86, 4076-4080 and U.S. Pat. Nos. 5,409,811 and 5,674,716, each of which is herein incorporated by reference in its entirety.

The term "nucleic acid," or "polynucleotide," as used herein, generally refers to a molecule comprising one or more nucleic acid subunits, or nucleotides. A nucleic acid may include one or more nucleotides selected from adenosine (A), cytosine (C), guanine (G), thymine (T) and uracil (U), or variants thereof. A nucleotide generally includes a nucleoside and at least 1, 2, 3, 4, 5, 6, 7, 8, 9, 10, or more phosphate ($PO_3$) groups. A nucleotide can include a nucleobase, a five-carbon sugar (either ribose or deoxyribose), and one or more phosphate groups.

Ribonucleotides are nucleotides in which the sugar is ribose. Deoxyribonucleotides are nucleotides in which the sugar is deoxyribose. A nucleotide can be a nucleoside monophosphate or a nucleoside polyphosphate (e.g., triphosphate). A nucleotide can be a deoxyribonucleoside polyphosphate, such as, e.g., a deoxyribonucleoside triphosphate (dNTP), which can be selected from deoxyadenosine triphosphate (dATP), deoxycytidine triphosphate (dCTP), deoxyguanosine triphosphate (dGTP), deoxyuridine triphosphate (dUTP) and deoxythymidine triphosphate (dTTP). A nucleotide can be a dideoxyribonucleoside polyphosphate, such as, e.g., a dideoxyribonucleoside triphosphate (ddNTP), which can be selected from dideoxyadenosine triphosphate (ddATP), dideoxycytidine triphosphate (ddCTP), dideoxyguanosine triphosphate (ddGTP), dideoxyuridine triphosphate (ddUTP) and dideoxythymidine triphosphate (ddTTP). A nucleotide may be a canonical nucleotide (e.g., may be of a canonical type). A nucleotide may be naturally occurring or an analog. For a given type of nucleotide, such analog may be naturally occurring but may not be non-canonical. The analog may be non-naturally occurring (e.g., synthesized). In some cases, dNTPs and/or ddNTPs may include detectable tags, such as luminescent tags or markers (e.g., fluorophores). A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). In some examples, a nucleic acid is deoxyribonucleic acid (DNA), ribonucleic acid (RNA), or derivatives or variants thereof. A nucleic acid may be single-stranded or double-stranded. In some cases, a nucleic acid molecule is circular.

The terms "nucleic acid molecule," "nucleic acid sequence," "nucleic acid fragment," "oligonucleotide" and "polynucleotide," as used herein, generally refer to a polynucleotide that may have various lengths, such as either deoxyribonucleotides or ribonucleotides (RNA), or analogs thereof. A nucleic acid molecule can have a length of at least about 10 bases, 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 50 kb, or more. An oligonucleotide is typically composed of a specific sequence of four nucleotide bases: adenine (A); cytosine (C); guanine (G); and thymine (T) (uracil (U) for thymine (T) when the polynucleotide is RNA). Thus, the term "oligonucleotide sequence" is the alphabetical representation of a polynucleotide molecule; alternatively, the term may be applied to the polynucleotide molecule itself. This alphabetical representation can be input into databases in a computer having a central processing unit and used for bio informatics applications such as functional genomics and homology searching. Oligonucleotides may include one or more nonstandard nucleotide(s), nucleotide analog(s) and/or modified nucleotides.

The term "nucleotide mixture," or "nucleotide solution", as used herein, refers to a collection of nucleotide molecules and/or nucleotide analogs. Nucleotide molecules of a nucleotide mixture may be naturally occurring nucleotide molecules and/or derivatives, analogs, or modified versions thereof. A collection of nucleotide molecules and/or nucleotide analogs may comprise one or more subsets of nucleotide molecules and/or nucleotide analogs. For example, a nucleotide mixture may comprise one or more subsets of nucleotide analogs. Nucleotide analogs of a subset of a nucleotide mixture may share one or more characteristics. For example, nucleotide analogs of a subset of a nucleotide mixture may each comprise a feature such as a reporter moiety. Similarly, nucleotide analogs of a subset of a nucleotide mixture may have one or more shared structural features. In some cases, a nucleotide mixture may comprise only a single canonical type of nucleotide or nucleotide analog. Alternatively, a nucleotide mixture may include two or three canonical types of nucleotides or nucleotide analogs, or more. One or more canonical types of nucleotides or nucleotide analogs may make up a majority of a nucleotide mixture. In one example, a nucleotide of a single canonical type (e.g., A) makes up the majority of a nucleotide mixture, with nucleotides of other canonical types (e.g., C, T, G) making up a minority of the nucleotide mixture. In another example nucleotides of two canonical types (e.g., A, G) make up the majority of a nucleotide mixture, with nucleotides of other canonical types (e.g., C, T) making up a minority of the nucleotide mixture. A nucleotide mixture may be of a given purity. A purity of a nucleotide mixture may describe the amount of a given canonical type of nucleotide present in a mixture relative to nucleotides of different canonical types. A nucleotide mixture may have at least 50%, 60%, 70%, 80%, 90%, 95%, 98%, 99%, 99.9%, 99.99% or greater purity.

Examples of modified nucleotides include, but are not limited to diaminopurine, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid(v), 5-methyl-2-thiouracil, 3-(3-amino-3-N-2-carboxypropyl) uracil, (acp3)w, 2,6-diaminopurine and the like. In some cases, nucleotides may include modifications in their phosphate moieties, including modifications to a triphosphate moiety. Non-limiting examples of such modifications include phosphate chains of greater length (e.g., a phosphate chain having, 4, 5, 6, 7, 8, 9, 10 or more phosphate moieties) and modifications with thiol moieties (e.g., alpha-thio triphosphate and beta-thiotriphosphates). Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain aminemodified groups, such as aminoallyl-dUTP (aa-dUTP) and aminohexylacrylamide-dCTP (aha-dCTP) to allow covalent attachment of amine reactive moieties, such as N-hydroxysuccinimide esters (NHS). Alternatives to standard (e.g., canonical) DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs compatible with natural and mutant polymerases for de novo and/or amplification synthesis are described in Betz K, Malyshev D A, Lavergne T, Welte W, Diederichs K, Dwyer T J, Ordoukhanian P, Romesberg F E, Marx A. Nat. Chem. Biol. 2012 July; 8(7):612-4, which is herein incorporated by reference for all purposes.

The term "sequencing," as used herein, generally refers to generating or identifying sequence of a biological molecule, such as a nucleic molecule. Sequencing may be single molecule sequencing or sequencing by synthesis. Sequencing may be massively parallel array sequencing (e.g., Illumina sequencing), which may be performed using template nucleic acid molecules immobilized on a support, such as a flow cell or beads.

The term "polymerase," as used herein, generally refers to any enzyme capable of catalyzing a polymerization reaction. Examples of polymerases include, without limitation, a nucleic acid polymerase. The polymerase can be naturally occurring or synthesized. In some cases, a polymerase has relatively high processivity. An example polymerase is a Φ29 polymerase or a derivative thereof. A polymerase can be a polymerization enzyme. In some cases, a transcriptase or a ligase is used (i.e., enzymes which catalyze the formation of a bond). Examples of polymerases include a DNA polymerase, an RNA polymerase, a thermostable polymerase, a wild-type polymerase, a modified polymerase, *E. coli* DNA polymerase I, T7 DNA polymerase, bacteriophage T4 DNA polymerase Φ29 (phi29) DNA polymerase, Taq polymerase, Tth polymerase, Tli polymerase, Pfu polymerase, Pwo polymerase, VENT polymerase, DEEPVENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tea polymerase, Tih polymerase, Tfi polymerase, Platinum Taq polymerases, Tbr polymerase, Tfl polymerase, Pfutubo polymerase, Pyrobest polymerase, Pwo polymerase, KOD polymerase, Bst polymerase, Bst 3.0 polymerase, Sac polymerase, Klenow fragment, polymerase with 3' to 5' exonuclease activity, and variants, modified products and derivatives thereof. In some cases, the polymerase is a single subunit polymerase. The polymerase can have high processivity, namely the capability of the polymerase to consecutively incorporate nucleotides into a nucleic acid template without releasing the nucleic acid template. In some cases, a polymerase is a polymerase modified to accept dideoxynucleotide triphosphates, such as for example, Taq polymerase having a 667Y mutation (see e.g., Tabor et al, PNAS, 1995, 92, 6339-6343, which is herein incorporated by reference in its entirety for all purposes). In some cases, a polymerase is a polymerase having a modified nucleotide binding, which may be useful for nucleic acid sequencing, with non-limiting examples that include ThermoSequenase polymerase (ThermoFisher), AmpliTaq FS (ThermoFisher) polymerase and Sequencing Pol polymerase (Jena Bioscience). In some cases, the polymerase is genetically engineered to have discrimination against dideoxynucleotides, such, as for example, Sequenase DNA polymerase (ThermoFisher).

The term "sample," as used herein, generally refers to a biological sample. Examples of biological samples include nucleic acid molecules, amino acids, polypeptides, proteins, carbohydrates, fats, or viruses. In some cases, the sample contains a target nucleic acid molecule. In an example, a biological sample is a nucleic acid sample including one or more nucleic acid molecules. In some examples, the biological sample is a nucleic acid sample including one or more target nucleic acid molecules. The target nucleic acid molecules may be cell-free or cell-free nucleic acid molecules, such as cell free DNA or cell free RNA. The target nucleic acid molecules may be derived from a variety of sources including human, mammal, non-human mammal, ape, monkey, chimpanzee, reptilian, amphibian, or avian, sources. Further, samples may be extracted from variety of animal fluids containing cell free sequences, including but not limited to blood, serum, plasma, vitreous, sputum, urine, tears, perspiration, saliva, semen, mucosal excretions, mucus, spinal fluid, amniotic fluid, lymph fluid and the like. Cell free polynucleotides may be fetal in origin (via fluid taken from a pregnant subject), or may be derived from tissue of the subject itself.

The term "mutation" or "mutated" as used herein generally refers to genetic mutations or sequence variations such as a point mutation, a single nucleotide polymorphism ("SNP"), an insertion, a deletion, a substitution, a transposition, a translocation, a copy number variation, or another genetic mutation, alteration or sequence variation.

The term "reporter moiety" as used herein, generally refers to a moiety that emits a signal that can be detected. In some cases, such a signal may be indicative of incorporation of one or more nucleotides or nucleotide analogs. In some cases, a reporter moiety is coupled to a nucleotide or nucleotide analog, which nucleotide or nucleotide analog may be used in a primer extension reaction. Coupling may be covalent or non-covalent (e.g., via ionic interactions, Van der Waals forces, etc.). Where covalent coupling is implemented, the reporter moiety may be coupled to the nucleotide or nucleotide analog via a linker, with non-limiting examples that include aminopropargyl, aminoethoxypropargyl, polyethylene glycol, polypeptides, fatty acid chains, hydrocarbon chains and disulfide linkages. In some cases, the linker is cleavable, such as photo-cleavable (e.g., cleavable under ultra-violet light), chemically-cleavable (e.g., via a reducing agent, such as dithiothreitol (DTT), tris(2-carboxyethyl)phosphine (TCEP)) or enzymatically cleavable (e.g., via an esterase, lipase, peptidase or protease). In some cases, the linker is non-cleavable.

In some examples, the reporter moieties comprise molecular structures that, once attached to a nucleic acid sequence, provide a distinct characteristic that is not inherent to those nucleic acid molecules. In some cases the reporter moieties create unique optical characteristics. In some cases, the reporter moieties can be used as a single signal generating entity or may be one of a pair of reporter moieties such that one reporter moiety performs the role of an energy donor, and the other reporter moiety performs the role of energy acceptor. Energy donors and/or energy acceptors can both be fluorophore molecules. Whether a fluorophore is a donor or an acceptor may be based on its excitation and emission spectra, and the fluorophore with which it is paired.

Examples of energy donor/energy acceptor fluorophore pairs include, but are not limited to, cyan fluorescent protein (CFP) and yellow fluorescent protein (YFP); Cy3 and Cy5; fluorescein and tetramethylrhodamine; IAEDANS and fluorescein; EDANS and dabcyl; fluorescein and QSY 7 or QSY 9 dyes; Alex Fluor 350 and Alexa Fluor 488; Alexa Fluor 488 and Alexa Fluor 546, 555, 568, 594, or 647; Alexa Fluor 568 and Alexa Fluor 647; and Alexa Fluor 594 and Alexa Fluor 85.

The term "quencher" as used herein generally refers to molecules that may be energy acceptors. Quencher molecules can be used with in some cases of the present method disclosed herein as acceptors of a dual reporter moiety structure. Example quenchers, without limitation, include Black Hole Quencher Dyes (Biosearch Technologies) such as BH1-0, BHQ-1, BHQ-3, BHQ-10); QSY Dye fluorescent quenchers (from Molecular Probes/Invitrogen) such QSY7, QSY9, QSY21, QSY35, and other quenchers such as Dabcyl and Dabsyl; Cy5Q and Cy7Q and Dark Cyanine dyes (GE Healthcare). Examples of fluorophore donor molecules that can be used in conjunction with above quenchers include, without limitation, fluorophores such as Cy3B, Cy3, or Cy5; Dy-Quenchers (Dyomics), such as DYQ-660 and DYQ-661; and ATTO fluorescent quenchers (ATTO-TEC GmbH), such as ATTO 540Q, 580Q, 612Q.

The term "nucleotide analog," as used herein, generally refers to an unnatural or non-naturally occurring nucleotide. A nucleotide analog may be detectable or undetectable. Examples of nucleotides and nucleotide analogs include, but are not limited to, thymidine triphosphate (TTP), deoxythymidine triphosphate (dTTP), deoxyuridine triphosphate (dUTP), 5-propynyl-2'-deoxyuridine 5'triphosphate (5-propynyl-dUTP), 5-bromo-2'-deoxyuridine 5'triphosphate (5-bromo-dUTP), 5-iodo-2'-deoxyuridine 5'triphosphate (5-iodo-dUTP), 5-ethynyl-2'-deoxyuridine 5'triphosphate (5-ethynyl-dUTP), 5-fluoro-2'-deoxyuridine 5'triphosphate (5-fluoro-dUTP), 5-proparylamino-2'-deoxyuridine 5'triphosphate (5-proparylamino-dUTP), 5-(oct-1,7-diynyl)-2'-deoxyuridine 5'triphosphate (5-octynyl-dUTP), deoxycytidine triphosphate (dCTP), 5-methyl-2'-deoxycytidine 5'triphosphate (5-methyl-dCTP), 5-bromo-2'-deoxycytidine 5'triphosphate (5-bromo-dCTP), 5-propynyl-2'-deoxycytidine 5'triphosphate (5-propynyl-dCTP), 5-ethynyl-2'-deoxycytidine 5'triphosphate (5-ethynyl-dCTP), 5-hydroxy-2'-deoxycytidine 5'triphosphate (5-hydroxy-dCTP), 5-hydroxymethyl-2'-deoxycytidine 5'triphosphate (5-hydroxymethyl-dCTP), 5-formyl-2'-deoxycytidine 5'triphosphate (5-formyl-dCTP), deoxyadenosine triphosphate (dATP), bromo-deoxyadenosine triphosphate, 7-deaza-7-iodo-2'-deoxyadenosine-5'-triphosphate (7-deaza-7-iodo-dATP), 7-deaza-2'-deoxyadenosine-5'-triphosphate (7-deaza-dATP), deoxyguanosine triphosphate (dGTP), iodo-2'-deoxyguanosine-5'-triphosphate (iodo-dGTP), 7-deaza-2'-deoxyguanosine-5'-triphosphate (7-deazadGTP), 5-Bromo-2'-deoxycytidine-5'-Triphosphate, 5-Propynyl-2'-deoxycytidine-5'-Triphosphate, 5-Ethynyl-2'-deoxycytidine-5'-Triphosphate, 5-Iodo-2'-deoxycytidine-5'-Triphosphate, 5-Methyl-2'-deoxycytidine-5'-Triphosphate, 5-Hydroxy-2'-deoxycytidine-5'-Triphosphate, 5-Aminoallyl-2'-deoxycytidine-5'-Triphosphate, 5-Hydroxymethyl-2'-deoxycytidine-5'-Triphosphate, 5-Propargylamino-2'-deoxycytidine-5'-Triphosphate, 5-Carboxy-2'-deoxycytidine-5'-Triphosphate, 5-Formyl-2'-deoxycytidine-5'-Triphosphate, 5-Bromo-2'-deoxyuridine-5'-Triphosphate, 5-Propynyl-2'-deoxyuridine-5'-Triphosphate, 5-Ethynyl-2'-deoxyuridine-5'-Triphosphate, 5-Iodo-2'-deoxyuridine-5'-Triphosphate, 5-Methyl-2'-deoxyuridine-5'-Triphosphate, 5-Hydroxy-2'-deoxyuridine-5'-Triphosphate, 5-Aminoallyl-2'-deoxyuridine-5'-Triphosphate, 5-Hydroxymethyl-2'-deoxyuridine-5'-Triphosphate, 5-Propargylamino-2'-deoxyuridine-5'-Triphosphate, 5-Carboxy-2'-deoxyuridine-5'-Triphosphate, 5-Formyl-2'-deoxyuridine-5'-Triphosphate, 7-deaza-7-Bromo-2'-deoxyguanosine-5'-Triphosphate, 7-deaza-7-Propynyl-2'-deoxyguanosine-5'-Triphosphate, 7-deaza-7-Ethynyl-2'-deoxyguanosine-5'-Triphosphate, 7-deaza-7-Iodo-2'-diguanosine-5'-Triphosphate, 7-deaza-7-Methyl-2'-deoxyguanosine-5'-Triphosphate, 7-deaza-7-Hydroxy-2'-deoxyguanosine-5'-Triphosphate, 7-deaza-7-Aminoallyl-2'-deoxyguanosine-5'-Triphosphate, 7-deaza-7-Hydroxymethyl-2'-deoxyguanosine-5'-Triphosphate, 7-deaza-7-Propargylamino-2'-deoxyguanosine-5'-Triphosphate, 7-deaza-7-carboxy-2'-deoxyguanosine-5'-Triphosphate, 7-deaza-7-Formyl-2'-deoxyguanosine-5'-Triphosphate, 7-deaza-7-Bromo-2'-deoxyadenosine-5'-Triphosphate, 7-deaza-7-Propynyl-2'-deoxyadenosine-5'-Triphosphate, 7-deaza-7-Ethynyl-2'-deoxyadenosine-5'-Triphosphate, 7-deaza-7-Iodo-2'-deoxyadenosine-5'-Triphosphate, 7-deaza-7-Methyl-2'-deoxyadenosine-5'-Triphosphate, 7-deaza-7-Hydroxy-2'-deoxyadenosine-5'-Triphosphate, 7-deaza-7-Aminoallyl-2'-deoxyadenosine-5'-Triphosphate, 7-deaza-7-Hydroxymethyl-2'-deoxyadenosine-5'-Triphosphate, 7-deaza-7-Propargylamino-2'-deoxyadenosine-5'-Triphosphate, 7-deaza-7-carboxy-2'-deoxyadenosine-5'-Triphosphate, and 7-deaza-7-Formyl-2'-deoxyadenosine-5'-Triphosphate.

In some cases, nucleotide analogs of a subset of nucleotide analogs of a nucleotide mixture may not be detectable by a detector. For example, in the case of an optical detector that collects optical signals, non-detectable nucleotide analogs may not comprise a dye, fluorophore, or other moiety (e.g., reporter moiety) that may render a nucleotide analog detectable. In another example, nucleotide analogs of a subset of nucleotide analogs of a nucleotide mixture may emit a signal however this signal may be below the detectable threshold of a detector.

In some examples, reporter moieties may be nucleic acid intercalator dyes. Examples include, but are not limited to ethidium bromide, YOYO-1, SYBR Green, and EvaGreen. The near-field interactions between energy donors and energy acceptors, between intercalators and energy donors, or between intercalators and energy acceptors can result in the generation of unique signals or a change in the signal amplitude. For example, such interactions can result in quenching (i.e., energy transfer from donor to acceptor that results in non-radiative energy decay) or Forster resonance energy transfer (FRET) (i.e., energy transfer from the donor to an acceptor that results in radiative energy decay).

Other examples of reporter moieties include electrochemical labels, electrostatic labels, colorimetric labels and mass tags. Such labels may be used with the systems and methods disclosed herein.

Systems

In an aspect, the present disclosure provides systems for processing a nucleotide mixture. FIG. 1 shows a system 100 comprising a first reaction space 101 and a second reaction space 102 for using methods of the present disclosure to process a nucleotide mixture. System 100 may be used to purify a solution, to perform nucleic acid synthesis, or to sequence a nucleic acid, for example. The system 100 may include a fluid flow unit for directing flow of a solution from the first reaction space 101 to the second reaction space 102. The system 100 may include an isolation unit for isolating the first reaction space 101 from the second reaction space 102. The isolation unit may be a valve, for example. The system may include one or more supports. Supports may have nucleic acid molecules immobilized thereto. Supports may be in the first reaction space 101, the second reaction space 102, or both.

The first reaction space 101 may be used to purify a solution prior to directing the solution to the second reaction space 102. A solution can be a nucleotide mixture. A nucleotide mixture can be of certain purity. For example, the first reaction space 101 may contain beads with nucleic acid molecules immobilized thereto. A nucleotide mixture may be directed to the first reaction space. Next, impurities from the nucleotide mixture (e.g., undesired nucleotides or nucleotide analogs) can be incorporated into the nucleic acid molecules immobilized to the beads. Impurities can be incorporated using a nucleic acid polymerase. The nucleic acid molecules may be designed such that impurities are primarily or exclusively incorporated. This incorporation can result in an increase in the purity of the nucleotide mixture. The second reaction space 102 may be used to further purify the solution or to perform nucleic acid synthesis (e.g., during sequencing, such as sequencing by synthesis).

Processing a Nucleotide Mixture

In an aspect, the present disclosure provides methods for processing a mixture. A mixture can be a nucleotide mixture. A nucleotide mixture can be of certain purity. Processing a mixture may comprise increasing the purity of a mixture. In some cases, processing can comprise incorporation of one or more nucleotides or nucleotide analogs from a nucleotide mixture (e.g., a subset of the mixture) into nucleic acid molecules coupled to a support in a reaction space. The support may be, for example, a flow cell, a planar surface, a volume matrix (e.g., a gel), a complex surface (e.g., fiberglass), or a particle (e.g., a bead). Incorporation can serve to increase the purity of a nucleotide mixture by reducing the amount of unwanted (e.g., contaminant) nucleotides or nucleotide analogs from a nucleotide mixture. Incorporation of one or more nucleotides or nucleotide analogs may comprise complementary nucleotide binding. Incorporation of one or more nucleotides or nucleotide analogs may comprise nucleic acid synthesis. Incorporation of one or more nucleotides or nucleotide analogs may comprise binding of a nucleotide or nucleotide analog to a complementary nucleotide or nucleotide analog on a single stranded nucleic acid molecule and nucleic acid polymerization, thereby generating a double-stranded nucleic acid molecule.

A method for processing a mixture (e.g., a nucleotide mixture) may comprise, in a first operation, selecting from a set of canonical types of nucleotides or nucleotides analogs a subset of canonical types of nucleotides or nucleotide analogs. Next, in a second operation, a mixture comprising a plurality of nucleotides or nucleotide analogs may be directed to a reaction space comprising a support having a plurality of nucleic acid molecules immobilized thereto. In some cases, the mixture can have a ratio of nucleotides or nucleotide analogs corresponding to the subset to all other nucleotides or nucleotide analogs in the mixture of greater than 1:1. In some cases, the mixture can have a ratio of nucleotides or nucleotide analogs corresponding to the subset to all other nucleotides or nucleotide analogs in the mixture of less than 1:1. In some cases, a percentage of nucleotides or nucleotide analogs corresponding to the subset relative to all other nucleotides or nucleotide analogs in the mixture is greater than 50%. In some cases, a percentage of nucleotides or nucleotide analogs corresponding to the subset relative to all other nucleotides or nucleotide analogs in the mixture is less than 50%. Next, in a third operation, nucleotides or nucleotide analogs from the mixture may be incorporated into the plurality of nucleic acid molecules. Nucleotides or nucleotide analogs that are incorporated may correspond to the subset selected in the first operation. Nucleotides or nucleotide analogs that are incorporated may not correspond to the subset selected in the first operation. Depending on the nature of the subset selected in the first operation, a ratio and/or percentage may be increased or decreased following incorporation. For example, a subset may contain A nucleotides, and the nucleotides or nucleotide analogs incorporated in the third operation may be G, T, and C nucleotides, thereby increasing the ratio of A nucleotides relative to all other nucleotides in the mixture. In another example, a subset may contain C, G, and A nucleotides, and the nucleotides or nucleotide analogs incorporated in the third operation may be C, G, and A nucleotides, thereby decreasing the ratio of C, G, and A nucleotides relative to all other nucleotides in the mixture. In some cases, the method can be performed in absence of sequencing or sequence identification of the plurality of nucleic acid molecules.

Figure 2:
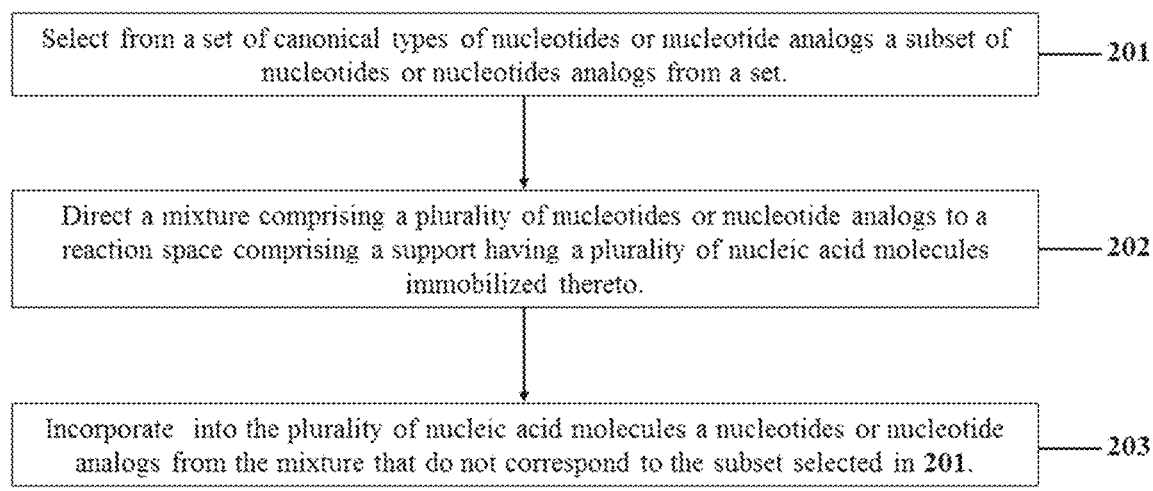
FIG. 2 shows a flowchart for a method of processing a mixture according to the present disclosure.

FIG. 2 shows flowchart of a method of processing a mixture of the present disclosure. In a first operation 201, a subset is selected from a set of canonical nucleotides or nucleotide analogs. For example, A nucleotides may be selected from a set of canonical nucleotides containing A, G, T, and C nucleotides. In a second operation 202, a mixture comprising a plurality of nucleotides or nucleotide analogs is directed to a reaction space comprising a support having a plurality of nucleic acid molecules immobilized thereto. The plurality of nucleotides or nucleotide analogs include those corresponding to the subset selected in operation 201. For example, the plurality of nucleotides or nucleotide analogs may include A nucleotides. In a third operation 203, nucleotides or nucleotide analogs from the mixture that do not correspond to the subset selected in 201 are incorporated into the plurality of nucleic acid molecules immobilized to the support. For example, if A nucleotides were selected in 201 from a set containing A, G, T, and C nucleotides, then G, T, and C nucleotides may be incorporated from the mixture into the nucleic acid molecules. In some cases, following incorporation in 203, the ratio of nucleotides or nucleotide analogs corresponding to the subset selected in 201 to all other nucleotides or nucleotide analogs in the mixture is increased relative to the original ratio of the mixture. In some cases, following incorporation in 203, the percentage of nucleotides or nucleotide analogs corresponding to the subset relative to all other nucleotides or nucleotide analogs in said mixture is increased relative to the original percentage of the mixture.

Figure 3:
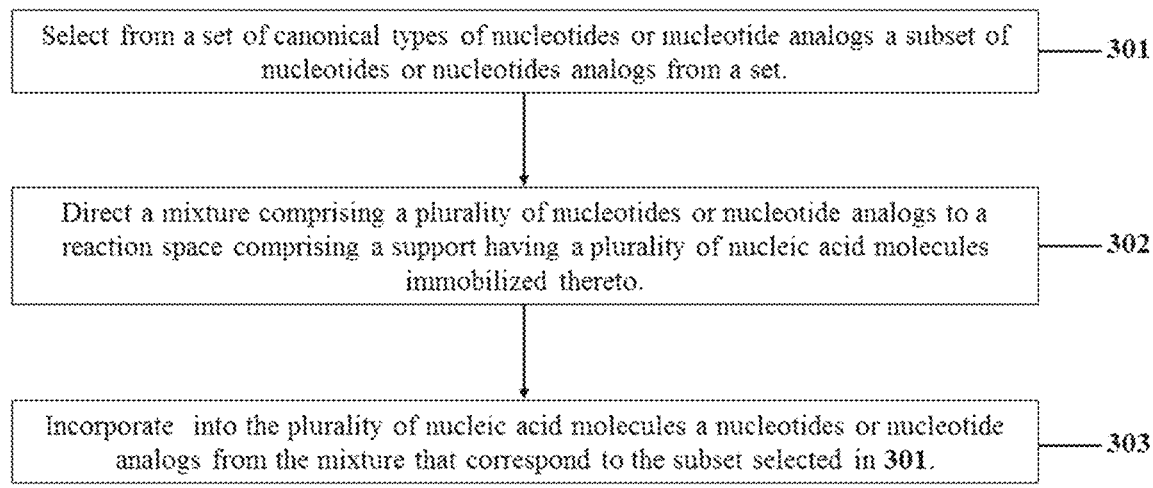
FIG. 3 shows a flowchart for a method of processing a mixture according to the present disclosure.

FIG. 3 shows flowchart of a method of processing a mixture of the present disclosure. In a first operation 301, a subset is selected from a set of canonical nucleotides or nucleotide analogs. For example, G, C, and T nucleotides may be selected from a set of canonical nucleotides containing A, G, T, and C nucleotides. In a second operation 302, a mixture comprising a plurality of nucleotides or nucleotide analogs is directed to a reaction space comprising a support having a plurality of nucleic acid molecules immobilized thereto. The plurality of nucleotides or nucleotide analogs include those corresponding to the subset selected in operation 301. For example, the plurality of nucleotides or nucleotide analogs may include G, C, and T nucleotides. In a third operation 303, nucleotides or nucleotide analogs from the mixture that correspond to the subset selected in 301 are incorporated into the plurality of nucleic acid molecules immobilized to the support. For example, if G, C, and T nucleotides were selected in 301 from a set containing A, G, T, and C nucleotides, then G, C, and T nucleotides may be incorporated from the mixture into the nucleic acid molecules. In some cases, following incorporation in 303, the ratio of nucleotides or nucleotide analogs corresponding to the subset selected in 301 to all other nucleotides or nucleotide analogs in the mixture is decreased relative to the original ratio of the mixture. In some cases, following incorporation in 303, the percentage of nucleotides or nucleotide analogs corresponding to the subset relative to all other nucleotides or nucleotide analogs in said mixture is decreased relative to the original percentage of the mixture.

A set of canonical types may comprise 1, 2, 3, 4, or 5 canonical types of nucleotides or nucleotide analogs. In some cases, a set of canonical types comprises A (e.g., dATP, ddATP, or a variant thereof), T (e.g., dTTP, ddTTP, or a variant thereof), G (e.g., dGTP, ddGTP, or a variant thereof), and C (e.g., dCTP, ddCTP, or a variant thereof) nucleotides. A subset selected from a set of canonical types may comprise one or more canonical types from the set, but not all canonical types from the set. For example, selecting a subset of nucleotides from a set of canonical types may comprise selecting an A nucleotide from a set comprising A, T, G, and C nucleotides. In another example, selecting a subset of nucleotides from a set of canonical types may comprise selecting A, G, and C nucleotides from a set comprising A, T, G, and C nucleotides.

In some cases, the ratio of nucleotides or nucleotide analogs corresponding to the selected subset to all other nucleotides or nucleotide analogs in a mixture is greater than 1:1, greater than 9:1, greater than 19:1, greater than 49:1, greater than 99:1, greater than 999:1, or greater. Following nucleotide or nucleotide analog incorporation as described herein, the ratio may increase by at least twofold, threefold, fourfold, fivefold, tenfold, twentyfold, fiftyfold, a hundredfold, a thousandfold, or more. For example, a subset may contain A nucleotides, a mixture may initially contain a ratio of A nucleotides to all other nucleotides of greater than 99:1, and, following incorporation, the ratio may be increased by at least tenfold. In some cases, the ratio of nucleotides or nucleotide analogs corresponding to the selected subset to all other nucleotides or nucleotide analogs in a mixture is less than 1:1, less than 1:9, less than 1:19, less than 1:49, less than 1:99, less than 1:999, or less. Following nucleotide or nucleotide analog incorporation as described herein, the ratio may decrease by at least twofold, threefold, fourfold, fivefold, tenfold, twentyfold, fiftyfold, a hundredfold, a thousandfold, or more. For example, a subset may contain A, G, and C nucleotides, a mixture may initially contain a ratio of A, G, and C nucleotides to all other nucleotides of less than 1:99, and, following incorporation, the ratio may be decreased by at least tenfold.

In some cases, the percentage of nucleotides or nucleotide analogs corresponding to the selected subset relative to all other nucleotides or nucleotide analogs in the mixture is greater than 50%, greater than 80%, greater than 90%, greater than 95%, greater than 99%, greater than 99.9%, greater than 99.99% or greater. Following nucleotide or nucleotide analog incorporation as described herein, the ratio may increase by at least twofold, threefold, fourfold, fivefold, tenfold, twentyfold, fiftyfold, a hundredfold, a thousandfold, or more. For example, a subset may contain A nucleotides, a mixture may initially contain a percentage of A nucleotides relative to all other nucleotides of greater than 99%, and, following incorporation, the percentage may be increased by at least tenfold. In some cases, the percentage of nucleotides or nucleotide analogs corresponding to the selected subset relative to all other nucleotides or nucleotide analogs in the mixture is less than 20%, less than 10%, less than 5%, less than 1%, less than 0.1%, less than 0.01%, less than 0.001%, or less. Following nucleotide or nucleotide analog incorporation as described herein, the percentage may decrease by at least twofold, threefold, fourfold, fivefold, tenfold, twentyfold, fiftyfold, a hundredfold, a thousandfold, or more. For example, a subset may contain A, G, and C nucleotides, a mixture may initially contain a percentage of A, G, and C nucleotides relative to all other nucleotides of less than 1%, and, following incorporation, the ratio may be decreased by at least tenfold.

Figure 10A:
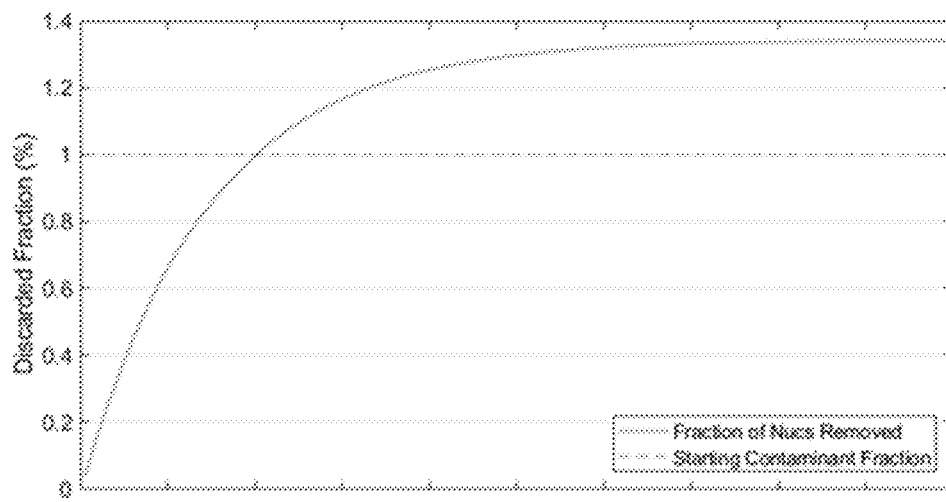
FIG. 10A and FIG. 10B show results from a Monte Carlo simulation of purifying a nucleotide mixture using methods described herein.
Figure 10B:
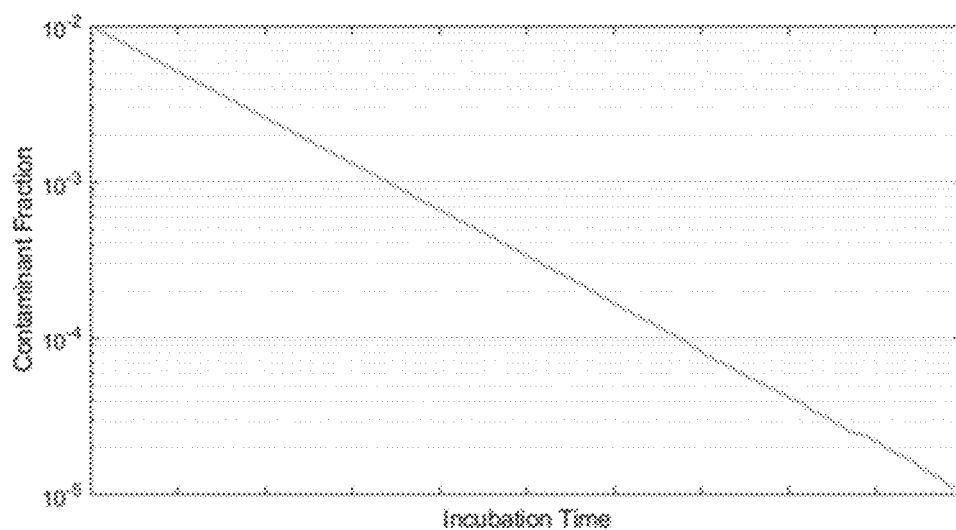

FIGS. 10A and 10B show a Monte Carlo simulation of an example method of purifying a nucleotide mixture as described herein. FIG. 10A shows the fraction of nucleotides ("Nucs") removed from a solution following incorporation into random nucleic acid molecules immobilized to a support. As the nucleotide solution increases in purity from 99% (far left) to 99.999% (far right), the amount of nucleotides removed from the solution increases to 1.35%. With a starting contamination fraction of 1% (dashed line), purification to 99.999% removes an additional 0.351% of the non-contaminant nucleotides in addition to 99.9% of the starting 1% of contaminant nucleotides. FIG. 10B shows the decrease in contaminant fraction with increasing incubation time (i.e. with increasing purity of the nucleotide solution) from 1% ($10^{-2}$) to 0.001% ($10^{-5}$).

Figure 11A:
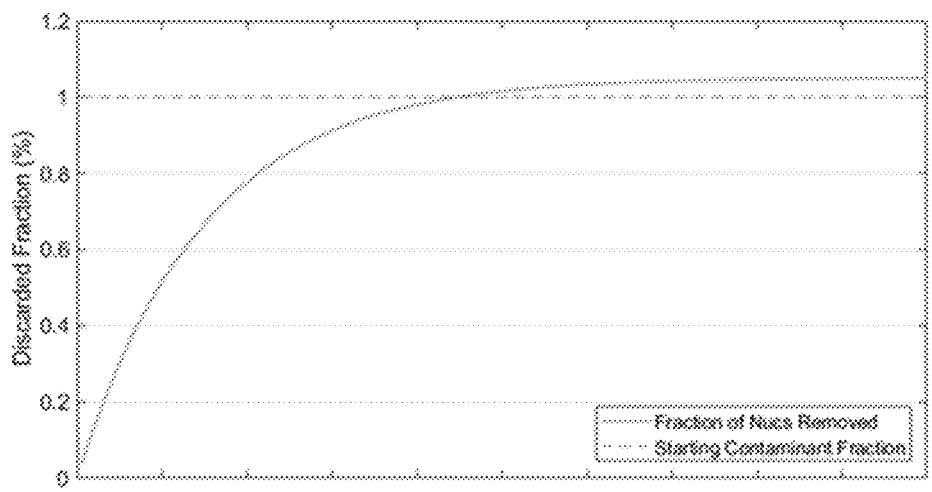
FIG. 11A and FIG. 11B show results from another Monte Carlo simulation of purifying a nucleotide mixture using methods described herein.
Figure 11B:
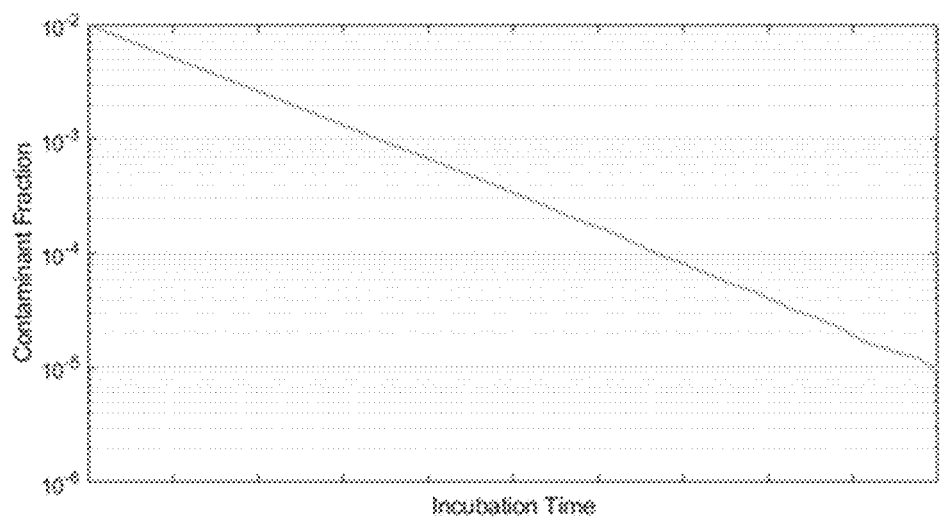

FIGS. 11A and 11B show a Monte Carlo simulation of an example method of purifying a nucleotide mixture as described herein. FIG. 11A shows, via a Monte Carlo simulation, the fraction of nucleotides ("Nucs") removed from a solution following incorporation into non-random nucleic acid molecules immobilized to a support. These non-random nucleotides were designed such that only 5% of their nucleotides are complementary to the canonical type of the primary nucleotide in the solution to be purified. In this example, as the nucleotide solution increases in purity from 99% (far left), to 99.999% (far right), the amount of nucleotides removed from the solution increases to 1.05%. Therefore, with a starting contamination fraction of 1% (dashed line), purification to 99.999% removes only an additional 0.05% of the non-contaminant nucleotides in addition to the 99.9% of the starting 1% of contaminant nucleotides. FIG. 11B shows the decrease in contaminant fraction with increasing incubation time (i.e. with increasing purity of the nucleotide solution) from 1% ($10^{-2}$) to 0.001% ($10^{-5}$).

Nucleotides or nucleotide analogs may be incorporated into a plurality of nucleic acid molecules containing nucleotides complementary to the nucleotides or nucleotide analogs that are incorporated. In some cases, the nucleic acid molecules contain a greater number of nucleotides complementary to nucleotides or nucleotide analogs which are incorporated relative to all other nucleotides. In some cases, the nucleic acid molecules do not contain nucleotides that are not complementary to the nucleotides or nucleotide analogs which are incorporated. In some cases, nucleotides or nucleotide analogs is incorporated using a nucleic acid polymerizing enzyme. The nucleic acid polymerizing enzyme may be a deoxyribonucleic polymerizing enzyme. The nucleic acid polymerizing enzyme may be capable of strand displacement. The nucleic acid polymerizing enzyme may be phi29 polymerase, Bst 3.0 polymerase, or a variant thereof.

Nucleic Acid Synthesis

Methods of the present disclosure may be used for nucleic acid synthesis. A method for synthesizing a nucleic acid molecule may comprise directing a plurality of nucleotides or nucleotide analogs to a first reaction space comprising a support having a plurality of nucleic acid molecules immobilized thereto. Next, a subset of nucleotides or nucleotide analogs from the plurality of nucleotides or nucleotide analogs can be incorporated into the plurality of nucleic acid molecules, thereby providing a remainder of the plurality of nucleotides or nucleotides analogs. Next, the remainder of the plurality of nucleotides or nucleotide analogs can be used to perform nucleic acid synthesis, thereby synthesizing a nucleic acid molecule. In some cases, the method can be performed in absence of sequencing or sequence identification of the plurality of nucleic acid molecules.

Figure 4:
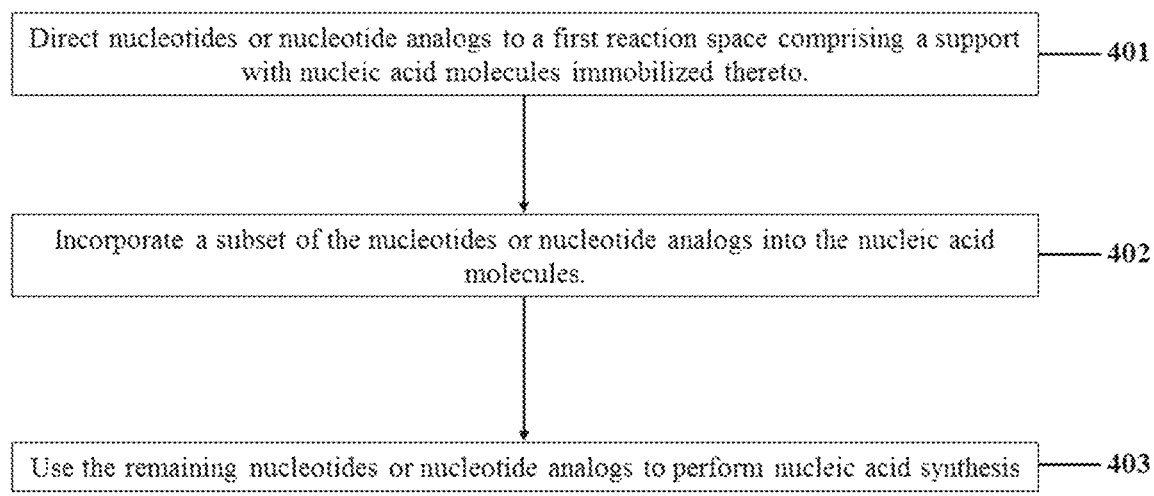
FIG. 4 shows a flowchart for a method of synthesizing a nucleic acid molecule according to the present disclosure.

FIG. 4 shows flowchart of a method of performing nucleic acid synthesis. In a first operation 401, nucleotides or nucleotide analogs are directed to a first reaction space comprising a support with nucleic acid molecules immobilized thereto. For example, a nucleotide mixture may be directed to a first reaction space comprising beads coupled to nucleic acid molecules. In a second operation 402, a subset of the nucleotides or nucleotide analogs is incorporated into the nucleic acid molecules, thereby providing a remainder of nucleotides or nucleotide analogs. In a third operation 403, the remainder of the nucleotides or nucleotide analogs is used to perform nucleic acid synthesis. For example, a nucleotide mixture may be removed from a first reaction space and provided to a second reaction space for nucleic acid synthesis.

In some cases, the nucleic acid synthesis can comprise nucleic acid sequencing. Canonical types in the subset of nucleotides or nucleotide analogs may be mutually exclusive from canonical types of the remainder in the plurality of nucleotides or nucleotide analogs. The subset of nucleotides or nucleotide analogs can be incorporated using a nucleic acid polymerizing enzyme. The nucleic acid polymerizing enzyme may be a deoxyribonucleic acid polymerizing enzyme.

Nucleic Acid Sequencing

Methods of the present disclosure may be used for nucleic acid sequencing. A method for sequencing a nucleic acid molecule may comprise directing a plurality of nucleotides or nucleotide analogs to a first reaction space comprising a support having a first plurality of nucleic acid molecules immobilized thereto. Next, a subset of nucleotides or nucleotide analogs from the plurality of nucleotides or nucleotide analogs may be incorporated into the first plurality of nucleic acid molecules, thereby providing a remainder of the plurality of nucleotides or nucleotides analogs. In some cases, incorporation of the subset of nucleotides or nucleotide analogs into the first plurality of nucleic acid molecules is performed without detecting the incorporation. Next, the remainder of the plurality of nucleotides or nucleotides analogs may be brought in contact with the nucleic molecule in a second reaction space. Next, at least a subset of the remainder of the plurality of nucleotides or nucleotides analogs may be incorporated into the nucleic acid molecule.

In some cases, incorporation of the at least the subset of the remainder of the plurality of nucleotides or nucleotide analogs may be detected. A sequence of the nucleic acid molecule may be determined subsequent to incorporating the at least the subset of the remainder of the plurality of nucleotides or nucleotides analogs into the target nucleic acid molecule. In some cases, the subset of nucleotides or nucleotide analogs is incorporated using a nucleic acid polymerizing enzyme. The nucleic acid polymerizing enzyme may be a deoxyribonucleic polymerizing enzyme. The nucleic acid polymerizing enzyme may be capable of strand displacement. The nucleic acid polymerizing enzyme may be phi29 polymerase, Bst 3.0 polymerase, or a variant thereof.

The plurality of nucleic acid molecules may contain nucleotides complementary to the subset of nucleotides or nucleotide analogs. The plurality of nucleic acid molecules may contain a greater number of nucleotides complementary to said subset of nucleotides or nucleotide analogs relative to all other nucleotides. The plurality of nucleic acid molecules may contain no nucleotides that are not complementary to the subset of nucleotides or nucleotide analogs. For example, the plurality of nucleic acid molecules may contain a greater number of each of A, T, and G nucleotides, relative to other nucleotides, where the subset of nucleotides or nucleotide analogs contains T, A, and C nucleotides.

The subset of nucleotides or nucleotide analogs can comprise less than 10%, less than 5%, less than 1%, less than 0.1%, less than 0.01%, or less than 0.001% of the plurality of nucleotides or nucleotide analogs. A nucleic acid molecule of a plurality of nucleic acid molecules may comprise a priming site. A priming site may be a primer. A primer may be covalently coupled to a nucleic acid molecule. A primer may allow for incorporation of nucleotides or nucleotide analogs using a nucleic acid polymerizing enzyme.

In some cases, the plurality of nucleotides or nucleotide analogs can include deoxynucleotides. The plurality of nucleotides or nucleotide analogs can include dideoxynucleotides. The subset of nucleotides or nucleotide analogs can include bases of a different type from the remainder. The support can be any support as described herein, such as a solid support, a gel matrix, fiberglass, a particle, a bead, etc. Incorporation of the subset of nucleotides or nucleotide analogs into the plurality of nucleic acid molecules can yield a remainder of nucleotides or nucleotide analogs with a purity that is increased relative to the purity of the original nucleotide mixture.

In some cases, incorporating nucleotides or nucleotide analogs into a plurality of nucleic acid molecules can yield double stranded nucleic acid molecules. A reaction space can be replenished with an additional plurality of nucleic acid molecules. A reaction space may be replenished by directing an additional support with an additional plurality of nucleic acid molecules immobilized thereto. A reaction space may be replenished by denaturation of double stranded nucleic acid molecules, thereby generating single stranded nucleic acid molecules. Single stranded nucleic acid molecules that are not immobilized to a support may be removed, thereby replenishing a reaction space.

Incorporation of nucleotides or nucleotide analogs into a nucleic acid can be detected by detecting one or more signals from the nucleic acid molecule upon incorporation of the nucleotides or nucleotide analogs. A signal may be an optical signal. An optical signal can be detected with an optical detector. A signal may be a charge change. A charge change may be a pH change. A charge change can be detected with, for example, an ion sensor or a voltage sensor. An ion sensor may be a pH sensor.

Figure 5:
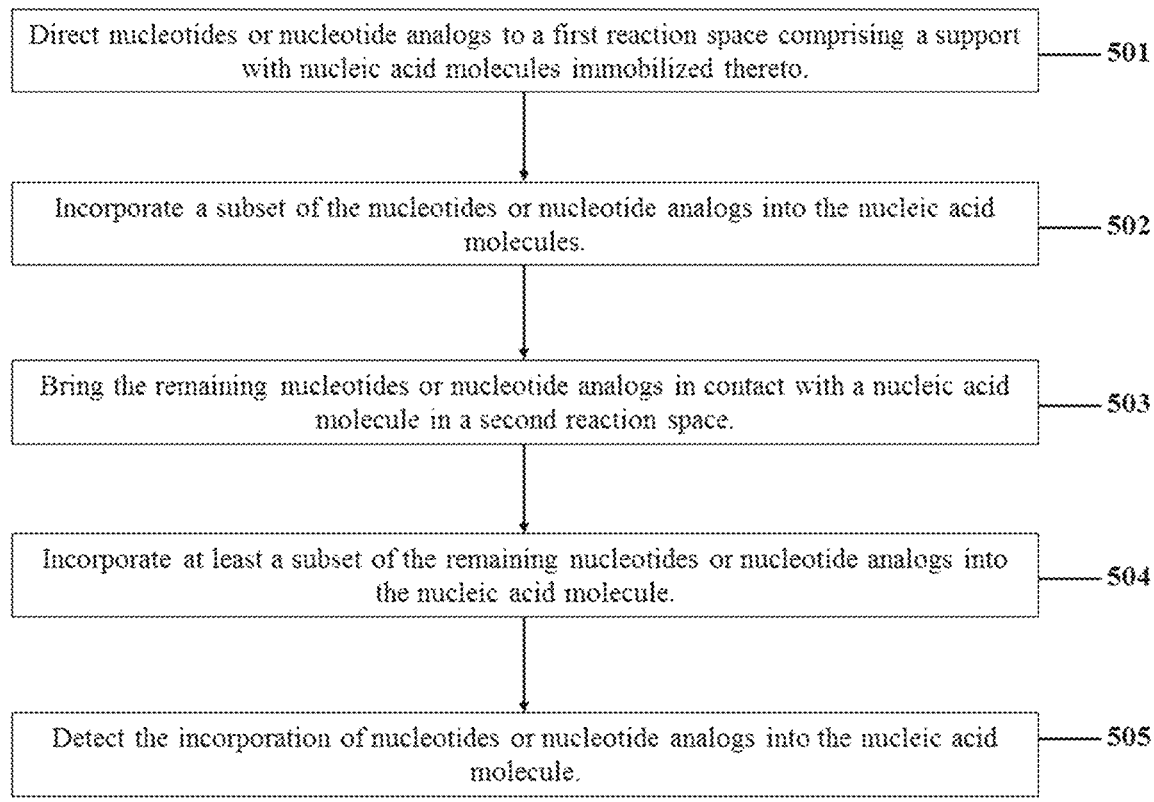
FIG. 5 shows a flowchart for a method of sequencing a nucleic acid molecule according to the present disclosure.

FIG. 5 shows an overview of an example method for nucleic acid sequencing of the present disclosure. In operation 501, nucleotides or nucleotide analogs (e.g., from a nucleotide mixture) are directed to a first reaction space comprising a support with nucleic acid molecules immobilized thereto. Nucleic acid molecules may comprise nucleotides or nucleotide analogs which are complementary to one or more of the nucleotides or nucleotide analogs in a mixture. In some cases, a nucleotide mixture may be separated and directed to more than one first reaction space. A nucleotide mixture may be separated into 1, 2, 3, 4, 5, or more first reaction spaces, each comprising a support with nucleic acid molecules immobilized thereto. In operation 504, a subset of the nucleotides or nucleotide analogs are incorporated into the nucleic acid molecules immobilized to the support. Nucleotides or nucleotide analogs may be incorporated by an enzyme. An enzyme may be a polymerase. An enzyme may have a preference for dNTPs compared to ddNTPs, which may prevent removal of ddNTPs required for sequencing from a nucleotide mixture. Operation 501 and 502 can be repeated 1, 2, 3, 4, 5, 6, 7, 8, 9, or 10 times, or more. Repeating operation 501 and 502 may serve to further increase the purity the nucleotide mixture. In operation 503, the remaining nucleotides or nucleotide analogs can be brought in contact with nucleic acid molecules in a second reaction space. The remaining nucleotides or nucleotide analogs may have a higher purity (e.g., reduced amount of undesired nucleotides or nucleotide analogs) than the original nucleotide mixture. The nucleic acid molecules in the second reaction space may be immobilized to a flow cell. The first reaction space and the second reaction space may be the same reaction space. For example, a single reaction space may comprise both a solid support (e.g., bead) as described herein and a sequencing flow cell, such that operations 502 and 503 are performed in a single reaction space. Alternatively, the first reaction space and the second reaction space may be different reaction spaces. In operation 504, at least a subset of the remaining nucleotides or nucleotide analogs is incorporated into the nucleic acid molecule. In operation 505, the incorporation of nucleotides or nucleotide analogs into the nucleic acid molecule is detected. Incorporation may be detected by measuring a signal. A signal may be a fluorescent signal. In some cases, the sequence of the nucleic acid molecules in the second reaction space can be determined. A sequence can be determined by, for example, nucleic acid sequencing (e.g., sequencing by synthesis), array hybridization, or polymerase chain reaction (e.g., qPCR, digital PCR, droplet PCR, etc.). A sequence can be determined by measuring the incorporation of labeled nucleotides or nucleotide analogs. For example, fluorescently labeled nucleotides or nucleotide analogs (e.g., using reporter moieties) may be used to identify a given base in a growing nucleic acid. Labeled nucleotides or nucleotide analogs may be terminating (e.g., may serve to stop the incorporation process for a given nucleic acid molecule). A nucleotide mixture processed via the methods of the present disclosure may be reused in subsequent reactions. A nucleotide mixture may be able to be reused due to a high purity as a result of the incorporation of undesired nucleotides (e.g., impurities) into nucleic acid molecules.

A nucleotide mixture of the present disclosure may comprise one or more nucleotides or nucleotide analogs (e.g., bases). In some cases, a nucleotide mixture can comprise an amount (e.g., a number, a concentration, etc.) of one or more types (e.g., canonical types) of nucleotides or nucleotide analogs (e.g., dATP, dGTP, dCTP, dTTP, dUTP, etc.). An amount of one or more types of nucleotides or nucleotide analogs may describe the purity of a nucleotide mixture. A nucleotide mixture can comprise at least about 50%, 60%, 70%, 80%, 90%, 95%, 98%, 99%, 99.5%, 99.9%, 99.99%, or more of one or more types of nucleotides or nucleotide analogs. In some examples, a nucleotide mixture can comprise greater than 99% of one type of nucleotide (e.g., dATP) and less than 1% of all other types of nucleotides (e.g., dGTP, dCTP, dTTP). In some examples, a nucleotide mixture can comprise greater than 99% of two types of nucleotides (e.g., dATP and dGTP) and less than 1% of all other types of nucleotides (e.g., dCTP and dTTP).

A nucleotide mixture can have a ratio of a number of nucleotides or nucleotide analogs of one or more types to nucleotides or nucleotide analogs of all other types. A ratio of nucleotides or nucleotide analogs of one or more types to nucleotides or nucleotide analogs of all other types can be at least 19:1, 29:1, 39:1, 49:1, 59:1, 69:1, 79:1, 89:1, 99:1, 999:1, 9999:1, or greater. In some examples, a nucleotide mixture can comprise a ratio of a number of nucleotides or nucleotide analogs of one type (e.g., dATP) to all other types (e.g., dGTP, dCTP, dTTP) of greater than 19:1. In some examples, a nucleotide mixture can comprise a ratio of a number of nucleotides or nucleotide analogs of two types (e.g., dATP and dGTP) to all other types (e.g., dCTP, dTTP) of greater than 19:1. A nucleotide mixture can comprise an amount of nucleotides or nucleotide analogs which are of different types than the remaining types of nucleotides or nucleotide analogs in the mixture. A nucleotide mixture can comprise at most about 5%, 1%, 0.1%, 0.01%, 0.001%, or less of nucleotides or nucleotide analogs of a different type. For example, a nucleotide mixture can comprise less than 1% of nucleotides which are not of a single type (e.g., dATP). In some examples, a nucleotide mixture can comprise less than 1% of nucleotides which are not of either of two types (e.g., dATP or dGTP).

Nucleotides or nucleotide analogs can be incorporated into nucleic acid molecules coupled to a support to reduce the amount of nucleotides or nucleotide analogs in a mixture which are of a different type than the remaining nucleotides or nucleotide analogs (e.g., to reduce impurities). Nucleotides or nucleotide analogs of a different type may be incorporated into nucleic acid molecules coupled to a support, thereby increasing the purity of a nucleotide mixture. Increasing the purity of a nucleotide mixture can be useful in, for example, nucleic acid synthesis and nucleic acid sequence identification. Increasing the purity of a nucleotide mixture may serve to concentrate the mixture for nucleic acid sequence identification. Increasing the purity of a nucleotide mixture can be useful in, for example, reducing phasing rate, reducing the cost of nucleic acid sequence identification, and allowing a nucleotide mixture to be reused. Phasing rates of nucleic acid sequencing as described herein may be at most about 1%, 0.1%, 0.01%, 0.001%, or less for a sequence having at least 50, 100, 150, 200, 250, 300, 400, 500, 1000, or more nucleotides.

In some aspects, the present disclosure provides methods for sequencing a nucleic acid molecule, wherein generating a sequence of a nucleic acid molecule is performed at a low phasing rate without resequencing the nucleic acid molecule. A method for sequencing a nucleic acid may comprise providing a nucleic acid molecule immobilized to a support. Next, a nucleic acid molecule can be brought in contact with a plurality of nucleotides or nucleotide analogs. The plurality of nucleotides or nucleotide analogs can have a ratio of a number of nucleotides or nucleotide analogs of one or more but less than all canonical types to a number of nucleotides or nucleotide analogs of all other canonical types which is greater than 19:1. Next, a sequence of the nucleic acid molecule can be determined at a phasing rate of at most 1% for a sequence of the nucleic acid molecule having a length of at least 50 nucleic acid bases without resequencing the nucleic acid molecule.

Figure 6:
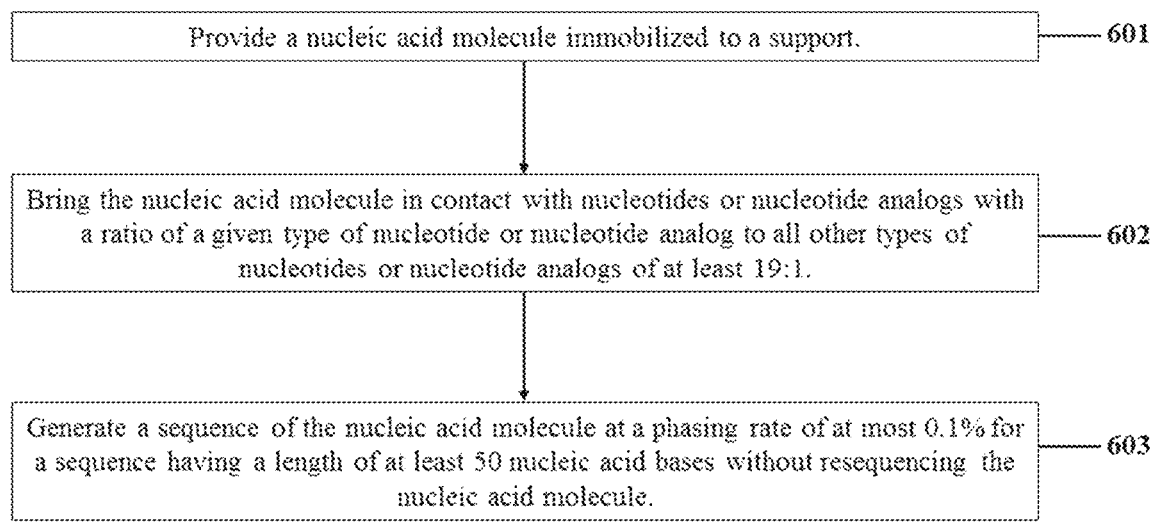
FIG. 6 shows a flowchart for another method of sequencing a nucleic acid molecule according to the present disclosure.

FIG. 6 shows an overview of an example method for nucleic acid sequencing of the present disclosure. In operation 601, a nucleic acid immobilized to a support is provided. A support may be a flow cell. In operation 602, a nucleic acid molecule is brought in contact with nucleotides or nucleotide analogs (e.g., a nucleotide mixture) with a ratio of a number of nucleotides or nucleotide analogs of one or more but less than all canonical types to a number of nucleotides or nucleotide analogs of all other canonical types which is greater than 19:1. A ratio of nucleotides or nucleotide analogs of one or more but less than all canonical types to a number of nucleotides or nucleotide analogs of all other canonical types can be at least 19:1, 29:1, 39:1, 49:1, 59:1, 69:1, 79:1, 89:1, 99:1, 999:1, 9999:1, or greater. A ratio of a given nucleotide or nucleotide analog to all other nucleotides or nucleotide analogs may be expressed as a purity of a nucleotide mixture. A nucleotide mixture can have a purity of at least 50%, 60%, 70%, 80%, 90%, 95%, 99%, 99.9%, 99.99%, or more. In operation 603, a sequence of the nucleic acid molecule is generated at a phasing rate of at most 1% for a sequence having a length of at least 50 nucleic acid bases. A sequence may be generated at a phasing rate of at most 0.1%, 0.01%, 0.001%, or less for a sequence having at least 50, 100, 150, 200, 250, 300, 400, 500, 1000, or more nucleotides.

A nucleic acid molecule may be brought into contact with one or more nucleotide mixtures to identify the sequence. A nucleic acid molecule may be brought into contact with at least 1, 2, 3, 4, 5, 10, 15, 20, 30, 40, 50, 100, 200 or more nucleotide mixtures. Each mixture can have a ratio of a number of nucleotides or nucleotide analogs of one or more but less than all canonical types to a number of nucleotides or nucleotide analogs of all other canonical types which is greater than 19:1. A nucleotide mixture primarily comprising one or more nucleotide or nucleotide analogs may be used multiple times. For example, a nucleotide mixture comprising primarily dGTP may be used each time a dGTP solution is needed to be brought into contact with a nucleic acid molecule for sequencing. Between uses, a nucleotide mixture may be processed (e.g., purified, concentrated) as described herein.

Supports

In some aspects, the present disclosure provides supports for use in the methods of the present disclosure. A support can be a solid support. A support can be a planar surface, a well surface, a bead, a particle, a gel particle, an aerogel particle, a polymer matrix, a fiberglass matrix, or a hydrogel particle. In some cases, a support with a high surface area to volume ratio may be used, which may serve to provide increased efficiency of nucleotide incorporation. A support may comprise one or more nucleic acid molecules immobilized thereto. Nucleic acid molecules may be immobilized to a support via covalent or non-covalent interactions. Nucleic acid molecules may be immobilized to a support directly, or may be attached to a molecule which is attached to the support. Nucleic acid molecules may be deoxyribonucleic acid molecules, ribonucleic acid molecules, or a combination thereof. Nucleic acid molecules can be single-stranded. Nucleic acid molecules can be double-stranded. Nucleic acid molecules can comprise a double-stranded region and a single-stranded region (e.g., single-stranded overhang). Nucleic acid molecules can comprise a nucleic acid primer. A nucleic acid primer can be used by an enzyme (e.g., a polymerase) to facilitate incorporation of nucleotides or nucleotide analogs into a nucleic acid molecule.

Figure 7:
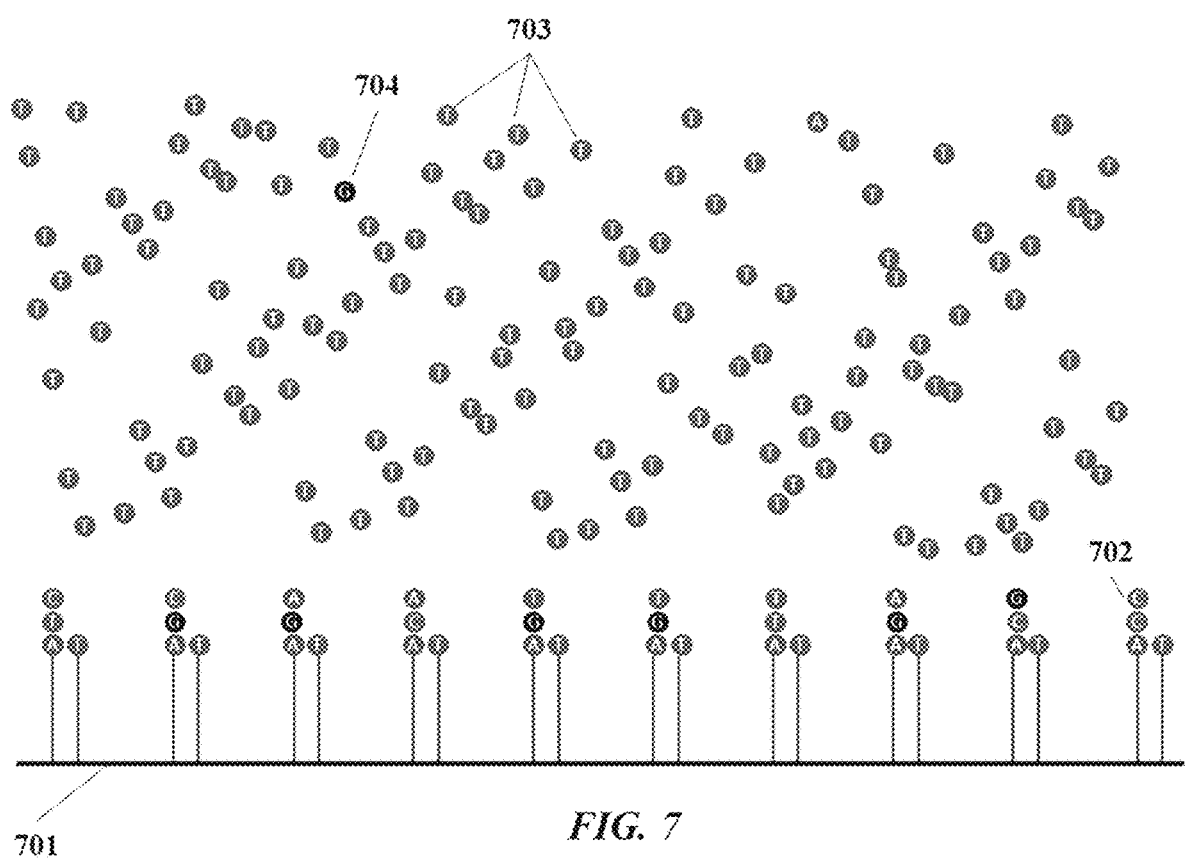
FIG. 7 schematically illustrates a nucleotide solution and primed linear nucleic acid molecules coupled to a support.

Nucleic acid molecules can be attached to a support in a linear fashion, wherein a single strand of a double-stranded nucleic acid molecule is attached to the support and a second strand is separate from and hybridized to the first strand (See FIG. 7). Nucleic acid molecules can be attached to a support in a hairpin fashion, such that a single strand of a nucleic acid molecule is attached to the support, and the nucleic acid molecule comprises a hairpin loop structure (See FIG. 8). Use of a support comprising nucleic acid molecules coupled thereto in a hairpin fashion may be useful in, for example, preventing the release of one or more nucleic acids from the support into a solution (e.g., a nucleotide solution). Nucleic acid molecules can be attached to a support in a ring structure (e.g., may be circular nucleic acid). For example, a nucleic acid molecule may be circular, with the molecule attached to the support via an internal attachment moiety, thereby creating a ring structure. A circular nucleic acid molecule may be attached to a support through hybridization to a nucleic acid molecule (e.g., a primer) attached to the support. FIG. 9 schematically illustrates an example of a circular nucleic acid molecule 901 attached to a support 903 via a primer 902.

Use of a support comprising nucleic acid molecules immobilized thereto in a ring structure may be useful in, for example, enabling large numbers of successive extension reactions without the need for replenishing the nucleic acid molecules. Use of a primer hybridized to a circular nucleic acid may, for example, retain the single stranded circular nucleic acid molecule coupled to the support throughout nucleotide incorporation, even with the use of large numbers of successive extension reactions.

Supports comprising nucleic acid molecules immobilized thereto may be useful in the methods of the present disclosure. Nucleotides or nucleotide analogs may be incorporated into nucleic acids immobilized to a support, in order to increase the purity of a solution (e.g., a nucleotide mixture). Nucleic acid molecules immobilized to a support may contain nucleotides complementary to a subset of nucleotides or nucleotide analogs to be incorporated from a nucleotide mixture. Nucleic acid molecules immobilized to a support may contain a greater number of nucleotides complementary to a subset of nucleotides or nucleotide analogs to be incorporated from a nucleotide mixture relative to all other nucleotides. Nucleic acid molecules immobilized to a support may contain exclusively nucleotides that are complementary to a subset of nucleotides or nucleotide analogs to be incorporated from a nucleotide mixture. In one example, when the subset of nucleotides or nucleotide analogs to be incorporated are A, G, and C nucleotides, nucleic acid molecules immobilized to a support may contain a greater number of each of T, C, and G nucleotides relative to the number of A nucleotides. In another example, when the subset of nucleotides or nucleotide analogs to be incorporated are A, and T nucleotides, nucleic acid molecules immobilized to a support may contain only T and A nucleotides, and no G or C nucleotides. The composition of nucleic acid molecules immobilized to a support may be varied depending on the solution (e.g., nucleotide mixture) to be purified. For example, a support may comprise nucleic acid molecules which comprise fewer A nucleotides, where such support may be useful in increasing the purity of a nucleotide mixture comprising primarily T nucleotides but with impurities in the form of other types of nucleotides or nucleotide analogs (e.g., G, C, T, U, etc.). Additional supports may comprise nucleic acid molecules which comprise fewer G, T, C, and/or U nucleotides. Each different support may be used to increase the purity of (e.g., to concentrate) a different nucleotide mixture.

Nucleotides or nucleotide analogs may be incorporated into nucleic acid molecules coupled to a support. Following one or more rounds of incorporation, nucleic acid molecules coupled to a support may be subjected to conditions sufficient for denaturation of the nucleic acid molecules. Denaturation may be chemical denaturation. Denaturation may be temperature denaturation (e.g., may comprise an increase in temperature). Following denaturation, regions of nucleic acid molecules which are not immobilized to the support (e.g., a single stranded nucleic acid molecule from a double-stranded nucleic acid molecule) may be removed, for example, by washing. Denaturation of nucleic acid molecules coupled to a support may be useful in, for example, increasing the number of available regions for nucleotide or nucleotide analog incorporation.

Nucleic acid molecules immobilized to a support can be monitored to determine the quantity of available regions for nucleotide or nucleotide analog incorporation. In some cases, labeled nucleotide analogs may be incorporated into nucleic acid molecules. Labeled nucleotide analogs may be fluorescently labeled. In some cases, intercalating dyes can be incorporated into nucleic acid molecules. Intercalating dyes may be fluorescent molecules which intercalate into double-stranded nucleic acid. Alternatively or in addition, fluorescently labeled nucleotides can be incorporated into nucleic acid molecules immobilized to a support. A signal (e.g., a fluorescence signal) may be used to determine the quantity of available regions for nucleotide or nucleotide analog incorporation. For example, an increase in the intercalating fluorescence intensity may indicate a reduction in the number of available single stranded regions. A given level of fluorescence intensity may indicate the need to replenish nucleic acid molecules immobilized to a support.

Supports of the present disclosure may comprise one or more enzymes. Enzymes can be attached to nucleic acid molecules. An enzyme may be a nucleic acid polymerizing enzyme (e.g., a deoxyribonucleic acid polymerase, a ribonucleic acid polymerase, etc.). A nucleic acid polymerizing enzyme may be capable of strand displacement. A nucleic acid polymerizing enzyme may be a phi29 polymerase, a Bst 3.0 polymerase, or a variant thereof. In cases where nucleic acid molecules immobilized to a support are denatured, an enzyme may be removed from the support. An enzyme may be added to a support following nucleic acid molecule denaturation.

FIG. 7 shows a schematic of an example support comprising nucleic acid molecules immobilized thereto. Support 701 is attached to nucleic acid molecules immobilized to the support in a linear fashion. Each nucleic acid molecule comprises a double-stranded and single-stranded region. Each nucleotide in the single-stranded region represents a region available for nucleotide or nucleotide analog incorporation. For example, nucleic acid molecule 702 comprises a double stranded region consisting of an A base and a T base hybridized together, and a single stranded region comprising two C nucleotides. The C nucleotides may be used to incorporate a complementary nucleotide or nucleotide analog (e.g., dGTP). Support 701 is in a reaction space comprising a nucleic acid mixture. The nucleic acid mixture comprises primarily dTTP molecules 703. The nucleic acid mixture also comprises a dGTP molecule 704. dGTP can be incorporated into nucleic acid 702, thereby increasing the purity of the nucleic acid mixture.

Figure 8:
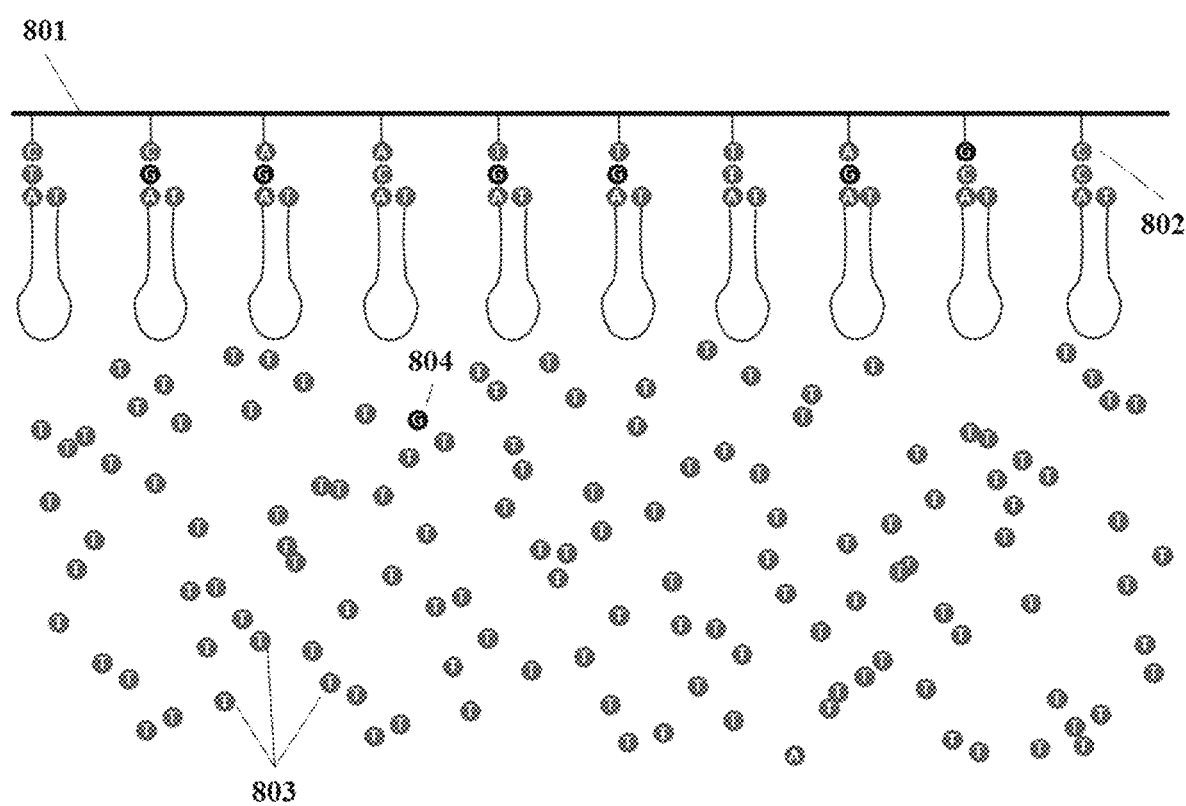
FIG. 8 schematically illustrates a nucleotide solution and primed hairpin nucleic acid molecules coupled to a support.
Figure 9:
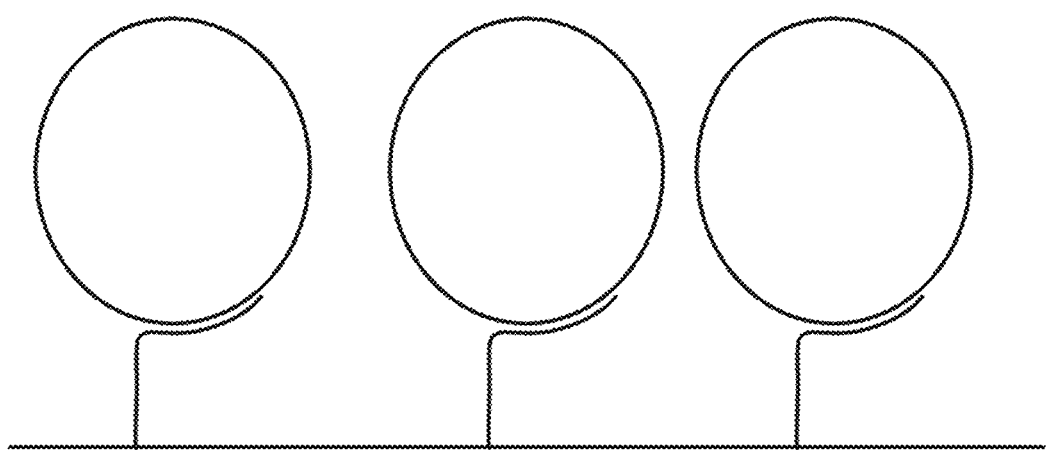
FIG. 9 schematically illustrates primed circular nucleic acid molecules coupled to a support.

FIG. 8 shows a schematic of an example support comprising nucleic acid molecules immobilized thereto. Support 801 is attached to nucleic acid molecules immobilized to the support in a hairpin fashion. Each nucleic acid molecule comprises a double-stranded and single-stranded region. Each nucleotide in the single-stranded region represents a region available for nucleotide or nucleotide analog incorporation. For example, nucleic acid molecule 802 comprises a double stranded region consisting of an A base and a T base hybridized together, and a single stranded region comprising two C nucleotides. The C nucleotides may be used to incorporate a complementary nucleotide or nucleotide analog (e.g., dGTP). Support 801 is in a reaction space comprising a nucleic acid mixture. The nucleic acid mixture comprises primarily dTTP molecules 803. The nucleic acid mixture also comprises a dGTP molecule 804. dGTP can be incorporated into nucleic acid 802, thereby increasing the purity of the nucleic acid mixture.

Computer Control Systems

Figure 12:
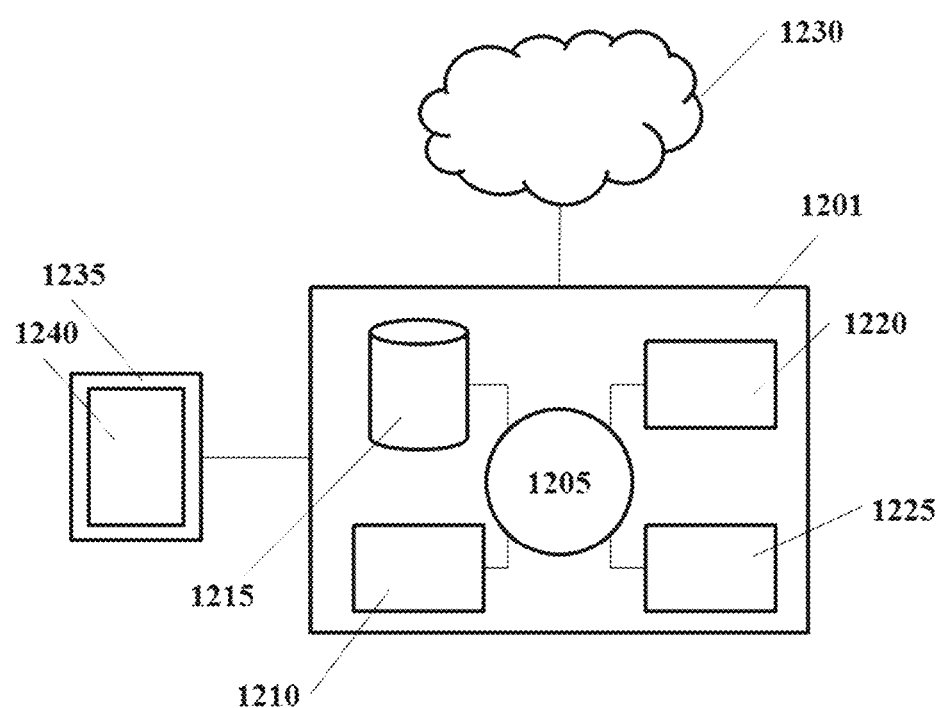
FIG. 12 shows a computer control system that is programmed or otherwise configured to implement methods or systems provided herein.

The present disclosure provides computer control systems that are programmed to implement methods of the disclosure. FIG. 12 shows a computer system 1201 that is programmed or otherwise configured to implement methods and systems of the present disclosure, such as performing nucleic acid sequence and sequence analysis.

The computer system 1201 includes a central processing unit (CPU, also "processor" and "computer processor" herein) 1205, which can be a single core or multi core processor, or a plurality of processors for parallel processing. The computer system 1201 also includes memory or memory location 1210 (e.g., random-access memory, read-only memory, flash memory), electronic storage unit 1215 (e.g., hard disk), communication interface 1220 (e.g., network adapter) for communicating with one or more other systems, and peripheral devices 1225, such as cache, other memory, data storage and/or electronic display adapters. The memory 1210, storage unit 1215, interface 1220 and peripheral devices 1225 are in communication with the CPU 1205 through a communication bus (solid lines), such as a motherboard. The storage unit 1215 can be a data storage unit (or data repository) for storing data. The computer system 1201 can be operatively coupled to a computer network ("network") 1230 with the aid of the communication interface 1220. The network 1230 can be the Internet, an internet and/or extranet, or an intranet and/or extranet that is in communication with the Internet. The network 1230 in some cases is a telecommunication and/or data network. The network 1230 can include one or more computer servers, which can enable distributed computing, such as cloud computing. The network 1230, in some cases with the aid of the computer system 1201, can implement a peer-to-peer network, which may enable devices coupled to the computer system 1201 to behave as a client or a server.

The CPU 1205 can execute a sequence of machine-readable instructions, which can be embodied in a program or software. The instructions may be stored in a memory location, such as the memory 1210. The instructions can be directed to the CPU 1205, which can subsequently program or otherwise configure the CPU 1205 to implement methods of the present disclosure. Examples of operations performed by the CPU 1205 can include fetch, decode, execute, and writeback.

The CPU 1205 can be part of a circuit, such as an integrated circuit. One or more other components of the system 1201 can be included in the circuit. In some cases, the circuit is an application specific integrated circuit (ASIC).

The storage unit 1215 can store files, such as drivers, libraries and saved programs. The storage unit 1215 can store user data, e.g., user preferences and user programs. The computer system 1201 in some cases can include one or more additional data storage units that are external to the computer system 1201, such as located on a remote server that is in communication with the computer system 1201 through an intranet or the Internet.

The computer system 1201 can communicate with one or more remote computer systems through the network 1230. For instance, the computer system 1201 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1201 via the network 1230.

Methods as described herein can be implemented by way of machine (e.g., computer processor) executable code stored on an electronic storage location of the computer system 1201, such as, for example, on the memory 1210 or electronic storage unit 1215. The machine executable or machine readable code can be provided in the form of software. During use, the code can be executed by the processor 1205. In some cases, the code can be retrieved from the storage unit 1215 and stored on the memory 1210 for ready access by the processor 1205. In some situations, the electronic storage unit 1215 can be precluded, and machine-executable instructions are stored on memory 1210.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1201 can include or be in communication with an electronic display 1235 that comprises a user interface (UI) 1240 for providing, for example, results of nucleic acid sequence (e.g., sequence reads, consensus sequences, etc.). Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1205. The algorithm can, for example, implement methods and systems of the present disclosure.

Kits

The present disclosure provides kits for use with methods and systems described herein. A kit can include one or more supports. The one or more supports may be one or more supports coupled to nucleic acid molecules as described herein. For example, a kit may include one or more beads, each coupled to nucleic acid molecules capable of incorporating nucleotides or nucleotide analogs. A kit can also include one or more nucleotide mixtures as described herein. A kit can include reagents and buffers necessary for performing the methods described herein. For example, a kit can include reagents for performing nucleic acid sequencing, or for purifying or concentrating reagents (e.g., mixtures), as disclosed herein. A kit can include a nucleic acid enzyme.

A kit can include a carrier, package, or container that may be compartmentalized to receive one or more containers, such as vials, tubes, and the like, each of the container(s) comprising one of the separate elements, such as the nucleic acid probes and buffers, to be used in a method described herein. Suitable containers include, for example, bottles, vials, syringes, and test tubes. The containers can be formed from a variety of materials such as glass or plastic.

The articles of manufacture provided herein contain packaging materials. Examples of packaging materials include, but are not limited to, bottles, tubes, bags, containers, or bottles. A kit can include labels listing contents of a kit and/or instructions for use, and package inserts with instructions for use. A set of instructions can also be included. The instructions may be in physical or digital format (e.g., instructions that may be included in a pamphlet or stored in computer memory).

EXAMPLES

Example 1: Nucleotide Solution Purification

Four nucleotide solutions are provided. A first nucleotide solution contains primarily dATP, a second contains primarily dCTP, a third contains primarily dTTP, and a fourth contains primarily dGTP. Each nucleotide solution contains additional, undesired nucleotides. The purity of each solution is less than 98%, and is therefore not usable for nucleic acid sequencing by synthesis. Beads with nucleic acid molecules immobilized thereto are provided to each solution. The nucleic acid molecules immobilized to the beads each comprise a priming site. The beads also comprise phi29 polymerase. Different types of beads are provided to each reagent. Beads containing nucleic acid molecules which do not comprise T nucleotides are provided to the third solution containing primarily dATP. Beads containing nucleic acid molecules which do not comprise G nucleotides are provided to the third solution containing primarily dCTP. Beads containing nucleic acid molecules which do not comprise A nucleotides are provided to the third solution containing primarily dTTP. Beads containing nucleic acid molecules which do not comprise C nucleotides are provided to the fourth solution containing primarily dGTP.

Each nucleotide solution is subjected to conditions sufficient to allow incorporation of nucleotides into the nucleic acid molecules immobilized to the beads using the phi29 polymerase. Each bead incorporates only undesired nucleotides. For example, beads provided to the solution containing primarily dATP do not incorporate dATP, but do incorporate other undesired nucleotides (e.g., dTTP, dCTP, dGTP, dUTP, etc.). This incorporation results in an increased purity of each nucleotide solution, such that the purity of each nucleotide solution is now greater than 99.99%. Due to the increased purity, nucleotide solutions are now able to be used for nucleic acid sequencing by synthesis.

Example 2: Nucleic Acid Sequencing with Low Phasing Rate

Four nucleotide solutions are provided. One nucleotide solution contains primarily dATP, a second contains primarily dCTP, a third contains primarily dTTP, and a fourth contains primarily dGTP. Each nucleotide solution contains additional, undesired nucleotides. Each nucleotide solution is placed in a first reaction chamber comprising beads with nucleic acid molecules immobilized thereto. The beads also comprise phi29 polymerase, and the nucleic acid molecules immobilized thereto comprise a priming site. The first reaction chamber is subjected to conditions sufficient to allow incorporation of nucleotides into the nucleic acid molecules immobilized to the beads using the phi29 polymerase. Following this, the purity of each nucleotide solution is increased relative to the starting value. Each nucleotide solution is such that the purity is greater than 99.99%.

Following purification, each nucleotide solution is provided to a flow cell comprising single-stranded nucleic acid molecules to be sequenced. Sequencing by synthesis is performed, thereby generating sequences of the nucleic acid molecules. Due to the high nucleotide solution purity, the sequence of the nucleic acid molecules attached to the flow cell is generated with a phasing rate of less than 0.1% without resequencing.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for processing a plurality of nucleic acid molecules, comprising:
   (a) directing a plurality of nucleotides or nucleotide analogs to a first reaction space comprising a support having a first plurality of nucleic acid molecules immobilized thereto;
   (b) incorporating a subset of nucleotides or nucleotide analogs from said plurality of nucleotides or nucleotide analogs into said first plurality of nucleic acid molecules, thereby providing a remainder of said plurality of nucleotides or nucleotide analogs, wherein (b) is performed in absence of detecting said subset of nucleotides incorporated into said first plurality of nucleic acid molecules;
   (c) bringing said remainder of said plurality of nucleotides or nucleotide analogs in contact with a second plurality of nucleic acid molecules in a second reaction space; and
   (d) incorporating at least a subset of said remainder of said plurality of nucleotides or nucleotide analogs into said second plurality of nucleic acid molecules.

2. The method of claim 1, further comprising detecting said at least said subset of said remainder of said plurality of nucleotides or nucleotide analogs incorporated into said second plurality of nucleic acid molecules.

3. The method of claim 1, wherein said subset of said remainder of said plurality of nucleotides or nucleotide analogs comprises nucleotides or nucleotide analogs of one or more but less than all base types.

4. The method of claim 1, wherein (b) is performed in absence of determining a sequence for any of said first plurality of nucleic acid molecules.

5. The method of claim 1, wherein said first plurality of nucleic acid molecules contains, at incorporation sites, nucleotides complementary to said subset of nucleotides or nucleotide analogs.

6. The method of claim 1, wherein said first plurality of nucleic acid molecules contains, at incorporation sites, a greater number of nucleotides complementary to said subset of nucleotides or nucleotide analogs from said plurality of nucleotides or nucleotide analogs in (b) relative to nucleotides of all other base types.

7. The method of claim 1, wherein said first plurality of nucleic acid molecules does not contain, at incorporation sites, nucleotides that are not complementary to said subset of nucleotides or nucleotide analogs.

8. The method of claim 1, wherein said subset of nucleotides or nucleotide analogs from said plurality of nucleotides or nucleotide analogs in (b) comprises less than 10%, less than 5%, less than 1%, less than 0.1%, or less than 0.01% of said plurality of nucleotides or nucleotide analogs.

9. The method of claim 1, wherein a nucleic acid molecule of said first plurality of nucleic acid molecules comprises a priming site.

10. The method of claim 1, wherein said plurality of nucleotides or nucleotide analogs comprises one or more nucleotides or nucleotide analogs selected from the group consisting of deoxynucleotides and dideoxynucleotides.

11. The method of claim 1, wherein said plurality of nucleotides or nucleotide analogs comprises nucleotides or nucleotide analogs selected from the group consisting of deoxyadenosine triphosphate (dATP), 2',3'-dideoxyadenosine-5'triphosphate (ddATP), deoxyguanosine triphosphate (dGTP), 2',3'-dideoxyguanosine-5'-triphosphate (ddGTP), deoxycytidine triphosphate (dCTP), 2',3'-dideoxycytidine-5'-triphosphate (ddCTP), deoxythymidine triphosphate (dTTP), 2',3'-dideoxythymidine-5'-triphosphate (ddTTP), deoxyuridine triphosphate (dUTP), 2',3'-dideoxyuridine-5'-triphosphate (ddUTP), and a variant thereof.

12. The method of claim 1, wherein said subset of nucleotides or nucleotide analogs from said plurality of nucleotides or nucleotide analogs in (b) includes bases of a different type from said remainder of said plurality of nucleotides or nucleotide analogs.

13. The method of claim 1, wherein said incorporating said subset of nucleotides or nucleotide analogs into said first plurality of nucleic acid molecules yields said remainder of said plurality of nucleotides or nucleotide analogs having a purity that is increased relative to a purity of said plurality of nucleotides or nucleotide analogs.

14. The method of claim 1, wherein said support comprises at least one planar surface.

15. The method of claim 1, wherein said first reaction space and said second reaction space are a same reaction space.

16. The method of claim 1, wherein said incorporating in (b) yields double stranded nucleic acid molecules from said first plurality of nucleic acid molecules comprising said subset of nucleotides or nucleotide analogs, and wherein, subsequent to (b), said first reaction space is replenished with an additional plurality of nucleic acid molecules, which additional plurality of nucleic acid molecules does not include said subset of nucleotides or nucleotide analogs.

17. The method of claim 16, wherein said first reaction space is replenished by denaturation of said double stranded nucleic acid molecules and removal of resultant single stranded nucleic acid molecules that are not immobilized to said support.

18. The method of claim 1, further comprising repeating (a)-(d) with at least one additional plurality of nucleotides or nucleotide analogs.

19. The method of claim 1, wherein said support is a solid support.

* * * * *